(12) United States Patent
Park et al.

(10) Patent No.: US 9,996,919 B2
(45) Date of Patent: Jun. 12, 2018

(54) METHOD FOR EXTRACTING AIRWAYS AND PULMONARY LOBES AND APPARATUS THEREFOR

(71) Applicant: Seoul National University R&DB Foundation, Seoul (KR)

(72) Inventors: Sang Joon Park, Seoul (KR); Jin Mo Goo, Seoul (KR); Jin Wook Chung, Seoul (KR); Doo Hee Lee, Gwangmyeong-si (KR); Yang Wook Kim, Seoul (KR)

(73) Assignee: SEOUL NATIONAL UNIVERSITY R&DB FOUNDATION, Seoul (KR)

( * ) Notice: Subject to any disclaimer, the term of this patent is extended or adjusted under 35 U.S.C. 154(b) by 131 days.

(21) Appl. No.: 14/909,304

(22) PCT Filed: Jun. 5, 2014

(86) PCT No.: PCT/KR2014/004989
§ 371 (c)(1),
(2) Date: Feb. 1, 2016

(87) PCT Pub. No.: WO2015/016481
PCT Pub. Date: Feb. 5, 2015

(65) Prior Publication Data
US 2016/0189373 A1    Jun. 30, 2016

(30) Foreign Application Priority Data

Aug. 1, 2013  (KR) ......................... 10-2013-0091595
Oct. 17, 2013  (KR) ......................... 10-2013-0124155

(51) Int. Cl.
*G06T 7/00* (2017.01)
*G06T 7/11* (2017.01)
(Continued)

(52) U.S. Cl.
CPC ............ *G06T 7/0012* (2013.01); *A61B 6/032* (2013.01); *A61B 6/466* (2013.01); *A61B 6/50* (2013.01);
(Continued)

(58) Field of Classification Search
None
See application file for complete search history.

(56) References Cited

U.S. PATENT DOCUMENTS 5,172,228 A * 12/1992 Israelsen ................... G06T 9/40
                                                              375/240.22
7,474,775 B2 * 1/2009 Abramoff ............ G06K 9/6277
                                                              351/206

(Continued)

FOREIGN PATENT DOCUMENTS

JP        2012223315 A    11/2012
KR  10-2012-0071292 A      7/2012
WO  WO 2007132487 A1 * 11/2007 ............. G06K 9/342

OTHER PUBLICATIONS

Pinho, Rômulo, Sten Luyckx, and Jan Sijbers. "Robust region growing based intrathoracic airway tree segmentation." Proc. of Second International Workshop on Pulmonary Image Analysis. 2009.*

(Continued)

*Primary Examiner* — Michelle M Entezari
(74) *Attorney, Agent, or Firm* — Brinks Gilson & Lione

(57) ABSTRACT

Provided is a method and apparatus for segmenting airways and pulmonary lobes. An image processing apparatus obtains a first candidate region of an airway from a three-dimensional (3D) human body image by using a region growing method, obtains a second candidate region of the airway based on a directionality of a change in signal intensity of voxels belonging to a lung region segmented from the 3D human body image, segments an airway region (Continued)

by removing noise based on similarity of a directionality of a change in signal intensity of voxels belonging to a third candidate region acquired by combining together the first and second candidate regions. Furthermore, the image processing apparatus segments a lung region from a 3D human body image by using a region growing method, obtains a fissure candidate group between pulmonary lobes based on a directionality of a change in signal intensity of voxels belonging to the lung region, reconstructs an image of the lung region including the fissure candidate group into an image viewed from a front side of a human body and generates a virtual fissure based on a fissure candidate group shown in the reconstructed image, and segments the pulmonary lobes by using the virtual fissure.

11 Claims, 33 Drawing Sheets

(51) Int. Cl.
*G06T 7/155* (2017.01)
*G06T 7/187* (2017.01)
*A61B 6/03* (2006.01)
*A61B 6/00* (2006.01)
*G06K 9/46* (2006.01)

(52) U.S. Cl.
CPC .............. *A61B 6/5211* (2013.01); *G06K 9/46* (2013.01); *G06T 7/11* (2017.01); *G06T 7/155* (2017.01); *G06T 7/187* (2017.01); *G06T 2207/10081* (2013.01); *G06T 2207/30061* (2013.01); *G06T 2207/30064* (2013.01)

(56) References Cited

U.S. PATENT DOCUMENTS

| | | | |
|---|---|---|---|
| 8,233,964 B2 | 7/2012 | Kiraly et al. | |
| 8,532,356 B2* | 9/2013 | Kiraly .................... | G06K 9/342 382/131 |
| 9,324,167 B2* | 4/2016 | Blaffert ................ | G01R 33/481 |
| 9,679,389 B2* | 6/2017 | Ostrovsky-Berman ... | G06T 7/11 |
| 2005/0063579 A1* | 3/2005 | Lee .......................... | G06K 9/34 382/131 |
| 2005/0207630 A1* | 9/2005 | Chan ...................... | A61B 6/466 382/131 |
| 2006/0247525 A1* | 11/2006 | Huo ...................... | G06T 7/0012 600/437 |
| 2009/0147001 A1* | 6/2009 | Buelow ..................... | G06T 7/11 345/424 |
| 2009/0208118 A1* | 8/2009 | Csurka ............... | G06K 9/00664 382/228 |
| 2009/0252394 A1* | 10/2009 | Liang ................. | G06K 9/00201 382/131 |
| 2010/0063410 A1* | 3/2010 | Avila ....................... | A61B 5/08 600/532 |
| 2011/0123085 A1* | 5/2011 | Sebok .................. | G06K 9/3216 382/132 |
| 2011/0243417 A1* | 10/2011 | Madabhushi ........ | G06K 9/3233 382/131 |
| 2012/0106821 A1* | 5/2012 | Madabhushi ......... | G06T 7/0012 382/133 |
| 2012/0163682 A1 | 6/2012 | Sohn et al. | |
| 2012/0268450 A1 | 10/2012 | Kiraly et al. | |
| 2013/0108133 A1 | 5/2013 | Inoue | |

OTHER PUBLICATIONS

Otsu, Nobuyuki. "A threshold selection method from gray-level histograms." IEEE transactions on systems, man, and cybernetics 9.1 (1979): 62-66.*

Frangi, Alejandro F., et al. "Multiscale vessel enhancement filtering." International Conference on Medical Image Computing and Computer-Assisted Intervention. Springer Berlin Heidelberg, 1998.*

Sato, Yoshinobu, et al. "3D multi-scale line filter for segmentation and visualization of curvilinear structures in medical images." CVRMed-MRCAS'97. Springer, Berlin, Heidelberg, 1997.*

Lorenz, Cristian, et al. "Multi-scale line segmentation with automatic estimation of width, contrast and tangential direction in 2D and 3D medical images." CVRMed-MRCAS'97. Springer, Berlin, Heidelberg, 1997.*

Jiang, Huiyan, et al. "A region growing vessel segmentation algorithm based on spectrum information." Computational and mathematical methods in medicine 2013 (2013).*

Xuejun Sun, PhD, et al., "3D Computerized Segmentation of Lung Volume With Computed Tomography", pp. 670-677, Dec. 21, 2005, H. Lee Moffitt Cancer Center and Research Institute, Department of Interdisciplinary Oncology, College of Medicine, University of South Florida.

International Search Report and Written Opinion issued in corresponding application PCT/KR2014/004989, dated Sep. 16, 2014, pp. 1-10.

Office Action issued in KR 10-2013-0124155, dated Nov. 4, 2014, pp. 1-5.

* cited by examiner (a)          (b)

(a)

(b)

(c)

(d)

METHOD FOR EXTRACTING AIRWAYS AND PULMONARY LOBES AND APPARATUS THEREFOR

CROSS-REFERENCE TO RELATED APPLICATIONS

This application a National Stage of International Application PCT/KR2014/004989 filed on Jun. 5, 2014, which claims the benefit of filing dates of Korean Patent Application No. 10-2013-0091595 filed on Aug. 1, 2013 and Korean Patent Application No. 10-2013-0124155 filed on Oct. 17, 2013. The entirety of all applications is hereby incorporated by reference.

TECHNICAL FIELD

The present invention relates to a method and apparatus for segmenting airways and pulmonary lobes from a three-dimensional (3D) image of a human body. The present invention is derived from research conducted as a part of the Science & Engineering Basic Research Project supported by the Ministry of Science, ICT, and Future Planning (MSIP) (Project No: 2014R1A1A1005264, Title: Detailed Classification of Korean COPD Severity Based on GOLD Criteria in Ultralow-dose Chest CT and Comparative Evaluation with Pulmonary Function Test: Multidisciplinary Development of Imaging Biomarker).

BACKGROUND ART

An airway through which air passes during breathing is composed of trachea and bronchi. A bronchus branches into very small bronchioles having a diameter less than or equal to 2 mm.

Accurate segmentation of airways is critical for correct analysis and determination of diseases of the bronchi and the chest using a computed tomography (CT) image. However, segmentation of the airways is difficult due to a partial volume effect and noise in a CT image and a decrease in contrast of signal intensity in an image, which is affected by lesions and organs adjacent to a bronchus. Thus, a conventional airway segmentation method is not able to provide good segmentation results for bronchioles having a diameter less than 2 mm.

Furthermore, human lungs consist of a right lung and a left lung. The right lung is separated into three lobes called upper, middle, and lower lobes by an oblique fissure and a horizontal fissure. The left lung has a smaller volume than the right lung and has two lobes, i.e., upper and lower lobes. Pulmonary lobes are separated from one another by a thin-film fissure less than 1 mm. When there is a need to remove a specific pulmonary lobe due to a lung disease through a surgical procedure or to determine accurate position information of an area affected by a lung disease before the surgical procedure, it is necessary to correctly identify and extract a 3D anatomical position of the specific pulmonary lobe separated by a fissure.

SUMMARY

To solve the inconvenience described above, an object of the present invention is to provide a method and apparatus for segmenting airways, which are capable of accurately segmenting even bronchioles having a very small diameter based on information about a tubular structure of a bronchial tree.

Another object of the present invention is to provide a method and apparatus for segmenting airways from a three-dimensional (3D) image of a human body by using an automated method without designation of a bronchus by a person.

Another object of the present invention is to provide a method and apparatus for delineating a fissure within the lung parenchyma from a 3D image of a human body and segmenting pulmonary lobes so that a user may precisely establish a medical/surgical treatment plan and a surgery plan by accurately analyzing and quantifying a position of a lesion of a lung disease.

According to an aspect of the present invention, there is provided a method of segmenting airways including: acquiring a three-dimensional (3D) human body image; obtaining a first candidate region of an airway from the 3D human body image by using a region growing method; segmenting a lung region from the 3D human body image and obtaining a second candidate region of the airway from the lung region based on a directionality of a change in signal intensities of voxels belonging to the lung region; obtaining a third candidate region by combining together the first and second candidate regions; and segmenting an airway region by removing noise based on similarity of a directionality of a change in signal intensity of voxels belonging to the third candidate region.

According to another aspect of the present invention, there is provided a method of segmenting airways including: acquiring a 3D human body image; setting an area having a width and a height of preset sizes in a sagittal plane of the 3D human body image; projecting a predetermined number of sagittal plane images located in the middle of the 3D human body image in a depth direction of the sagittal plane into a single image; searching for a voxel having a lowest signal intensity among voxels belonging to the set area in the single image and setting the found voxel as a seed point; and segmenting an airway by using a region growing method based on the seed point.

According to an aspect of the present invention, there is provided a method of segmenting pulmonary lobes, including: acquiring a 3D human body image; segmenting a lung region from the 3D human body image by using a region growing method; obtaining a fissure candidate group between the pulmonary lobes based on a directionality of a change in signal intensity of voxels belonging to the lung region; reconstructing an image of the lung region including the fissure candidate group into an image viewed from a front side of a human body and generating a virtual fissure based on the fissure candidate group shown in the reconstructed image; and segmenting the pulmonary lobes by using the virtual fissure.

According to another aspect of the present invention, there is provided a method of segmenting pulmonary lobes, including: acquiring a 3D human body image; segmenting a lung region from the 3D human body image by using a region growing method; obtaining a virtual fissure between the pulmonary lobes in the lung region; calculating coordinates of a centroid of each of regions separated by the virtual fissure; and segmenting the pulmonary lobes by performing the region growing method simultaneously on each of the regions by using the coordinates of the centroid of each of the regions as a seed point.

According to the present invention, it is possible to maximize detection of bronchial segments, which extend from trachea having a length of about 30 mm to bronchioles having a diameter less than or equal to 2 mm, in a 3D chest image without omission by using information about a tubular structure of a bronchial tree. Furthermore, it is possible to automatically determine a starting position for segmentation of airways in a 3D human body image.

Furthermore, a pulmonary lobe may be segmented without omission in a low-dose CT using a radiation dose that is over 10 times less than that of high resolution CT. In addition, a fissure formed of a thin film having a thickness less than 1 mm between pulmonary lobes may be correctly identified using anatomical information, and anatomical information of a lesion within the lung parenchyma may be provided by accurately segmenting five (5) pulmonary lobes within the long parenchyma

DETAILED DESCRIPTION

Hereinafter, a method and apparatus for segmenting airways, according to the present invention, will be described with reference to the accompanying drawings.

Figure 1:
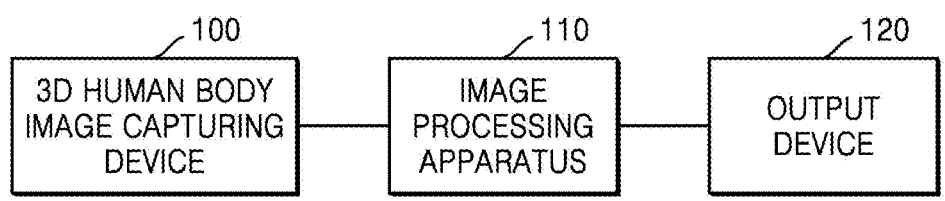
FIG. 1 is a schematic diagram of a system for capturing and processing a three-dimensional (3D) human body image according to an exemplary embodiment of the present invention.

FIG. 1 is a schematic diagram of a system for capturing and processing a three-dimensional (3D) human body image according to an exemplary embodiment of the present invention.

Referring to FIG. 1, the system according to the present invention includes a 3D human body image capturing device 100, an image processing apparatus 110, and an output device 120.

The 3D human body image capturing device 100 is a device for capturing 3D images of internal parts of a human body, and is generally a computed tomography (CT) apparatus or magnetic resonance imaging (MRI) apparatus. However, examples of the 3D human body image capturing device 100 are not limited thereto, and include all devices capable of obtaining a 3D image of an internal area of the human body.

The image processing apparatus 110 receives a 3D human body image captured by the 3D human body image capturing device 100 and processes the received 3D human body image according to various purposes such as segmenting of desired tissue. Although FIG. 1 shows that the image processing apparatus 110 receives a 3D human body image directly from the 3D human body image capturing device 100, exemplary embodiments are not limited thereto, and the image processing apparatus 110 may receive a 3D human body image stored in various electronic media (e.g., Compact Discs (CDs), Digital Versatile Discs (DVDs), Universal Serial Bus (USB) memory, etc.).

The output device 120 generally includes a monitor and receives and outputs an image of a human body's tissue processed by the image processing apparatus 110. The output device 120 and the image processing apparatus 110 may be implemented as a single device, or the output device 120 may be connected to the image processing apparatus 110 via wired and wireless communication networks and display an image received from the image processing apparatus 110.

While exemplary embodiments disclosed herein relate to a method and apparatus for segmenting airways and pulmonary lobes among tissues of the human body from a 3D human body image, they are provided only for understanding of the present invention and convenience of explanation, and the present invention is not limited thereto. The method and apparatus may be used to segment other tissues in the human body based on the basic concept of the present invention.

Figure 2:
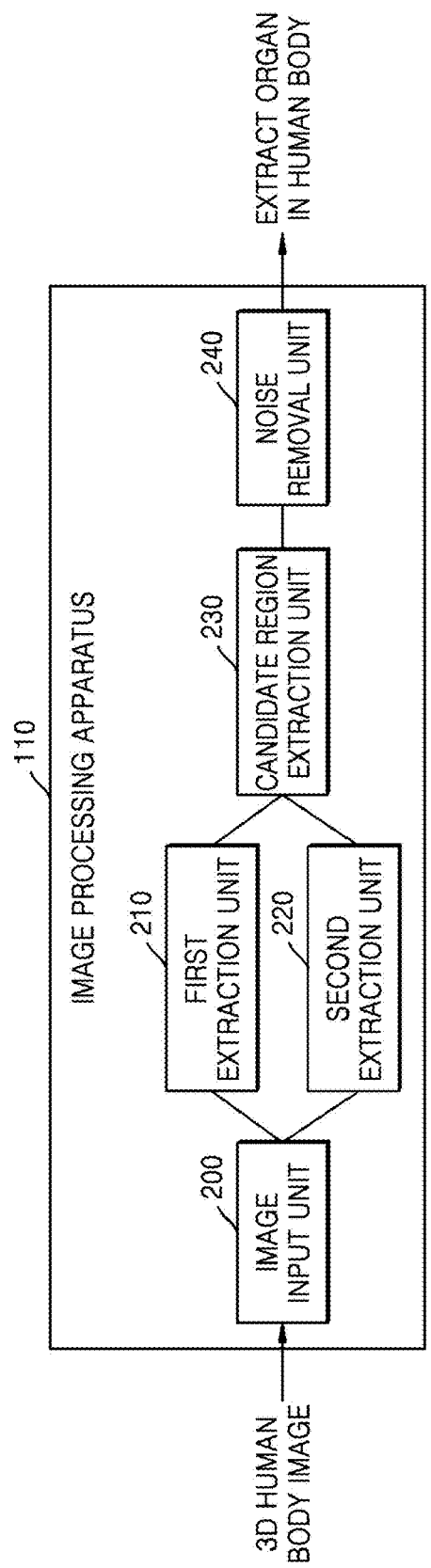
FIG. 2 is a diagram of a configuration of an image processing apparatus for segmenting airways from a 3D human body image, according to an exemplary embodiment of the present invention.

FIG. 2 is a diagram of a configuration of an image processing apparatus 110 for segmenting airways from a 3D human body image, according to an exemplary embodiment of the present invention.

Referring to FIG. 2, the image processing apparatus 110 includes an image input unit 200, a first extraction unit 210, a second extraction unit 220, a candidate region extraction unit 230, and a noise removal unit 240.

The image input unit 200 receives a 3D human body image. The 3D human body image shows each tissue as contrast of signal intensity. For example, in a CT image, signal intensity of lung tissue is less than or equal to about −400 Hounsfield Units (HU), while signal intensity inside the airway filled with air is defined as about −950 HU.

The first extraction unit 210 obtains a first candidate region of an airway by applying a region growing method to a 3D human body image. In this case, a simple region growing or adaptive region growing method may be used as the region growing method.

A simple region growing method is a method of expanding a region to neighboring regions that satisfy upper and lower limit values of signal intensity from a 3D pixel point, i.e., a voxel, belonging to a human body's tissue to be segmented. For example, lower and upper limit values of signal intensity for segmenting airways from a CT image may be −1024 HU and −950 HU, respectively.

Since signal intensity for the same tissue in a 3D human body's image varies slightly from person to person or depending on the disease, upper and lower limit values for using a region growing method need to be changed properly in order to more accurately segment tissues of the human body. A method of segmenting tissue by using an adaptive region growing method will be described in detail below with reference to FIG. 9.

An initial point for region growing, i.e., a seed point, has to be determined to apply a simple or adaptive region growing method. The seed point may be selected directly by a person, but the present exemplary embodiment proposes a method of automatically determining a seed point, as described below with reference to FIGS. 4 through 7.

Since the first candidate region is obtained by the first extraction unit 210 simply via contrast of signal intensity, it is difficult to accurately segment bronchioles having a diameter less than or equal to 2 mm. Furthermore, if a 3D human body image has low resolution, which means that a very small number of voxels represent the bronchioles, it is much more difficult to segment the bronchioles.

To accurately segment bronchioles having a diameter less than or equal to 2 mm, the second extraction unit 220 first segments a lung region from a 3D human body image and then obtains a second candidate region for a bronchus based on the directionality of a change in signal intensity of voxels belonging to the lung region. A human body's tissue may have structural characteristics that are distinct from those of neighboring regions. For example, a bronchial tree has a tubular structure, and vectors representing a change in signal intensity are aligned in a specific direction due to the tubular structure. A method of segmenting tissue via the second extraction unit 220 based on the directionality of a change in signal intensity of voxels will be described in detail below with reference to FIGS. 12 and 13.

The candidate region extraction unit 230 acquires a third candidate region by combining together the first and second candidate regions respectively obtained by the first and second extraction units 210 and 220. For example, the candidate region extraction unit 230 obtained a third candidate region by connecting the first and second candidate regions with each other. For this purpose, the candidate region extraction unit 230 may obtained the third candidate region of an airway by applying a region growing method to a single image obtained by combining together the first and second candidate regions.

The noise removal unit 240 removes noise in the third candidate region obtained by the candidate region extraction unit 230 to segment a final airway image. The noise removal unit 240 removes noise based on similarity in the directionality of a change in signal intensity from voxels belonging to the third candidate region. A method of removing noise will be described in detail below with reference to FIGS. 14 through 16.

Figure 3:
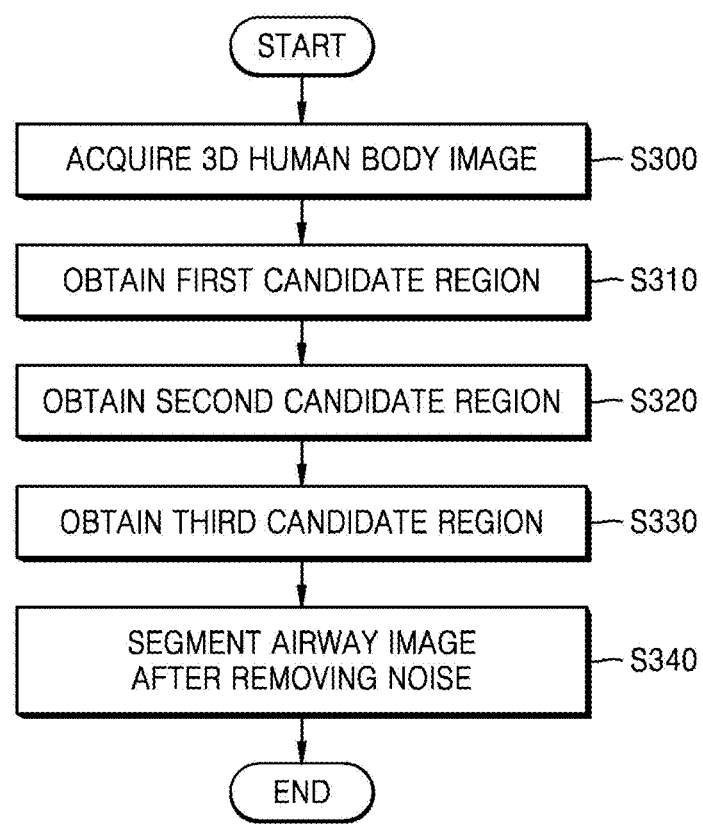
FIG. 3 is a flowchart of a method of segmenting airways from a 3D human body image, according to an exemplary embodiment of the present invention.

FIG. 3 is a flowchart of a method of segmenting airways from a 3D human body image, according to an exemplary embodiment of the present invention.

Figure 9:
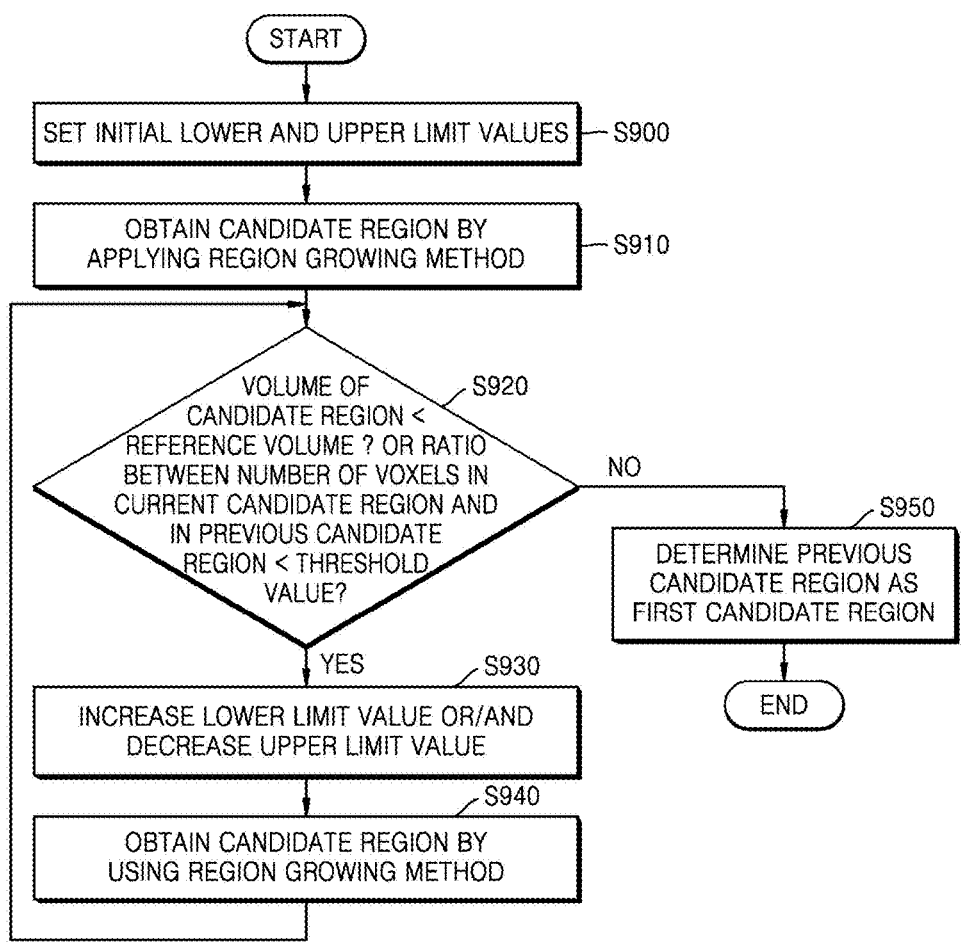
FIG. 9 is a flowchart of an adaptive region growing method according to an exemplary embodiment of the present invention.

Referring to FIG. 3, first, an image processing apparatus receives a 3D human body image (S300). The image processing apparatus then obtains a first candidate region of an airway by applying a region growing method to the received 3D human body image (S310). FIG. 9 illustrates an adaptive region growing method of obtaining a first candidate region, and FIG. 4 illustrates a method of automatically determining a seed point for using a region growing method.

Next, the image processing apparatus segments a lung region from the received 3D human body image and obtains a second candidate region based on the directionality of a change in signal intensity of voxels belonging to the lung region (S320). A method of obtaining a second candidate region will be described in detail with reference to FIG. 12.

The image processing apparatus obtains a third candidate region by applying a region growing method to an image obtained by combining together the first and second candidate regions (S330). The image processing apparatus then removes noise from the obtained third candidate region to obtain a final airway image (S340). Removal of noise will be described in detail with reference to FIGS. 14 through 16.

Figure 4:
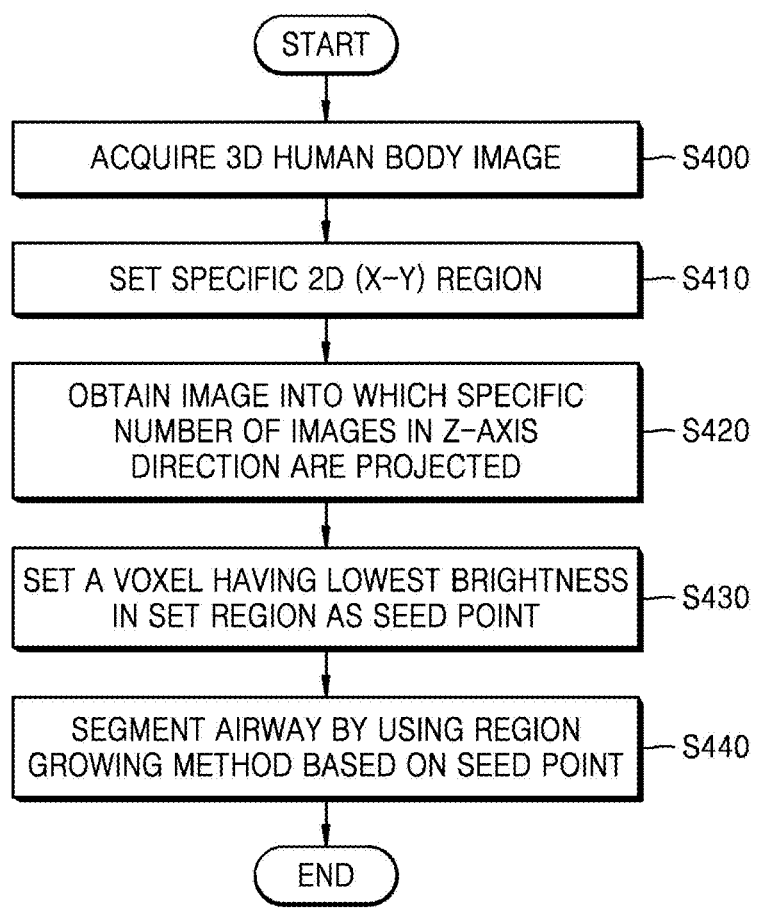
FIG. 4 is a flowchart of a method of automatically determining a seed point for a region growing method, according to an exemplary embodiment.
Figure 5:
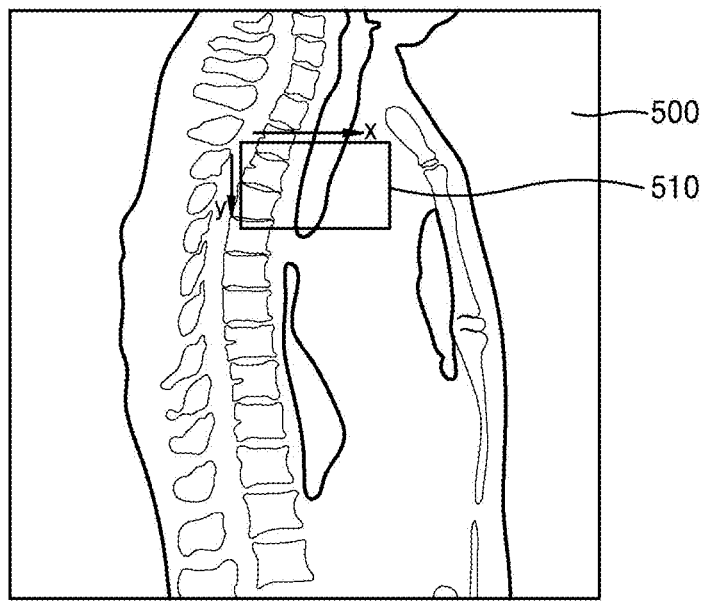
FIGS. 5 through 7 illustrate an example where a method of determining a seed point is applied to segmentation of airways.
Figure 6:
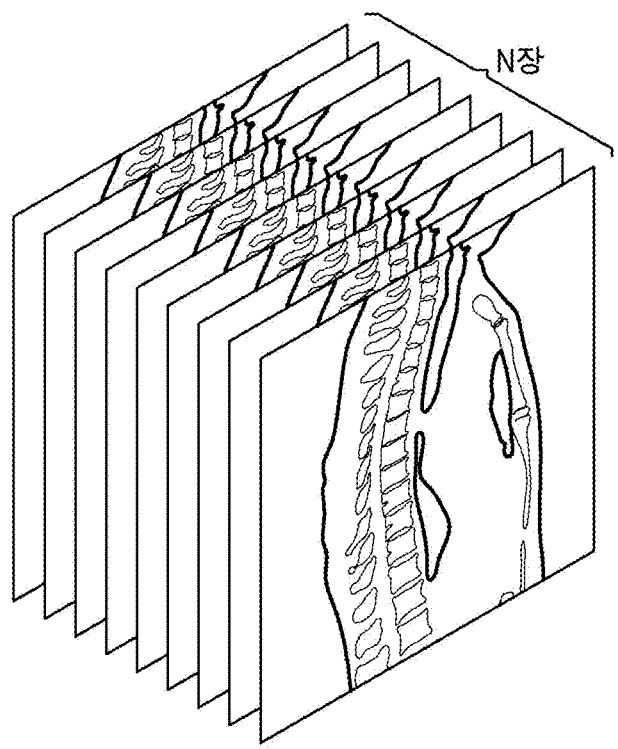
Figure 7:
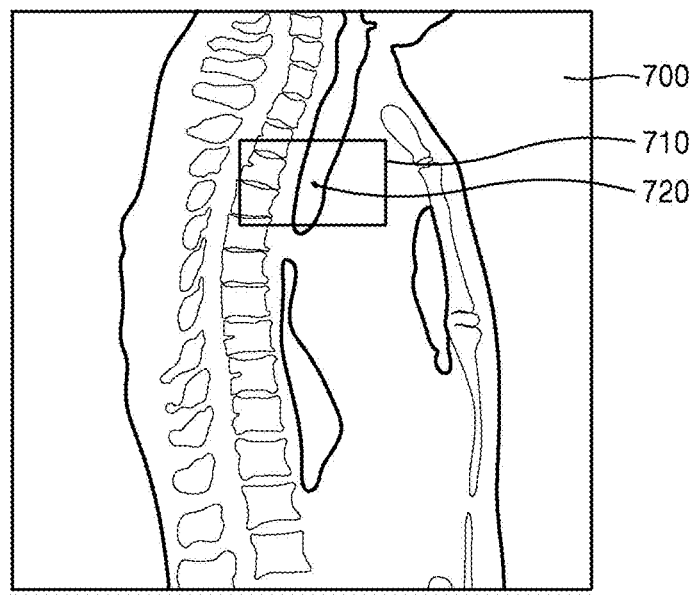

FIG. 4 is a flowchart of a method of automatically determining a seed point for a region growing method, according to an exemplary embodiment. FIGS. 5 through 7 illustrate an example where a method of determining a seed point is applied to segmentation of airways.

Referring to FIG. 4, an image processing apparatus receives a 3D human body image (S400). The image processing apparatus defines a size and a location of a 2D region within the received 3D human body image (S410). The size and location of the 2D region may be predetermined according to a portion depicted in the 3D human body image and an anatomical position of tissue to be segmented and stored. For example, if an airway is to be segmented from a CT image, as shown in FIG. 5, the imaging processing apparatus may define, based on a sagittal plane image 500 in a 3D chest image, a 2D reference region 510 having a width of 50 pixels in left and right directions from a center of a horizontal x-axis and a height determined by connecting a point that is a distance corresponding to 30% to 40% of the total length of a vertical y-axis. Since a center of the x-y plane in a CT image is almost fixed while a center of z-axis may always vary, a 2D reference region may be set based on a sagittal plane.

The image processing apparatus selects a specific number of images in a depth (z-axis) direction of the 2D (x-y) region and then projects the specific number of images into a single image (S420). For example, if an airway is to be segmented, as shown in FIG. 6, the image processing apparatus may select a number N (e.g., 10) images located in the middle of sagittal plane human body images in the z-axis direction and project them into a single sagittal plane image (700 of FIG. 7). For example, if the resolution in the z-axis direction is 512 pixels, the image processing apparatus may project ten (10) images, i.e., 251-th to 260-th sagittal plane images in the z-axis direction.

The image processing apparatus selects as a seed point a voxel having a specific signal intensity in the previously set 2D reference region in the single image obtained by projecting the N images (S430). For example, if a seed point 720 is to be determined for segmentation of an airway, the image processing apparatus selects a voxel having the lowest signal intensity in a 2D reference region 710 as the seed point 720 since a space inside the airway is filled with air and has very low signal intensity. To verify whether the selected seed point 720 is present in tissue to be segmented, the image processing apparatus determines whether the number of voxels connected to the seed point and having similar signal intensity is greater than or equal to a predetermined threshold. When the number of voxels connected to the seed point 720 is less than the predetermined threshold, the image processing apparatus determines that selection of the seed point is wrong, searches for another neighboring voxel, and selects the found neighboring voxel as a seed point.

The image processing apparatus may segment desired tissue, e.g., an airway by using a region growing method based on an automatically determined seed point (S440).

Figure 8:
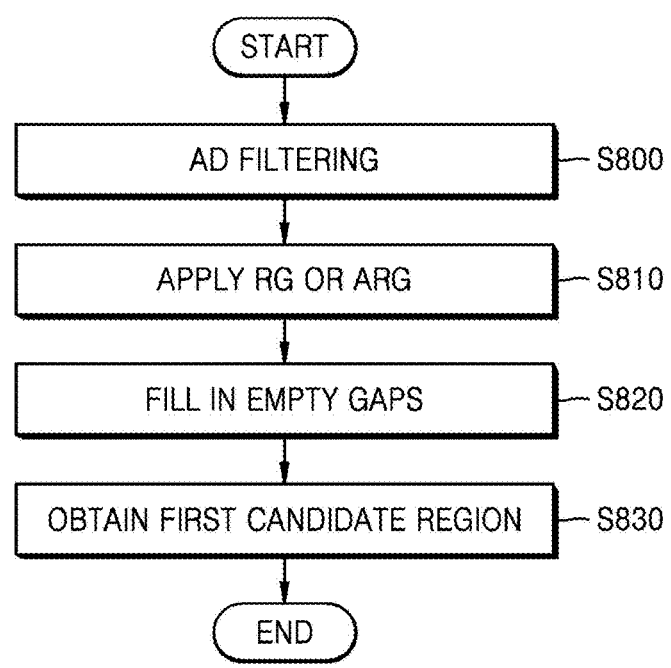
FIG. 8 is a detailed flowchart of a method of obtaining a first candidate region for segmenting airways, according to the present invention.

FIG. 8 is a detailed flowchart of a method of obtaining a first candidate region for segmenting airways, according to the present invention. The method of FIG. 8 corresponds to an operation of the first extraction unit 210 described above with reference to FIG. 2 or step S310 of obtaining a first candidate region in the method of FIG. 3.

Referring to FIG. 8, the image processing apparatus may perform a preprocessing step for removing noise before using a region growing method when necessary (S800). For example, the image processing apparatus may perform anisotropic diffusion (AD) filtering during the preprocessing step. The AD filtering has been conventionally widely used as a reliable algorithm for effectively removing noise while preserving an edge, and thus, a detailed description thereof will be omitted below. In the AD filtering, the number i of iterations and a filtering strength k need to be determined. For example, i and k may be set to 1 and $\infty$, respectively.

After performing the preprocessing step, the image processing apparatus segments a region by using a region growing method (a simple or adaptive region growing method) (S810). For example, the image processing apparatus may segment an airway region by using a region growing method based on a seed point within an organ in a 3D chest image.

Figure 11:
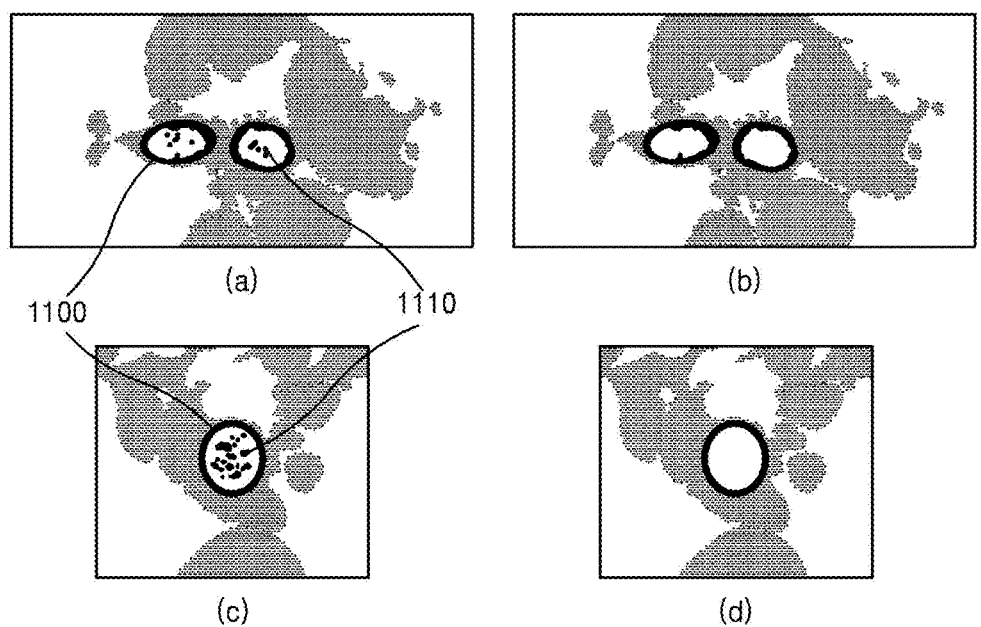
FIG. 11 illustrates a gap in an airway region segmented using a region growing method and a result of filling in the gap, according to an exemplary embodiment.

If a specific region is segmented using a region growing method, noise such as an empty gap may be contained in the specific region, as shown in FIG. 11. For example, if airway regions 1100 are segmented using a region growing method, as shown in FIG. 11, empty gaps 1110 may be present in the airway regions 1100 (See (a) and (c) of FIG. 11). Thus, the image processing apparatus removes noise such as the empty gaps 1110 (S820). Various algorithms are used to fill in empty gaps within a segmented image. For example, the image processing apparatus may fill in empty gaps within a segmented region by performing a morphological closing operation with a structuring element (SE) according to Equation (1) below (See (b) and (d) of FIG. 11).

$$I^b = I_S \cdot B_{26} = (I_S \oplus B_{26}) \ominus B_{26} \qquad \text{Equation (1)}$$

In Equation (1), I is a binary reconstruction image obtained by using a region growing method and $B_{26}$ is a round SE consisting of 26 neighboring pixels around a central pixel Thereby, the image processing apparatus acquires a first candidate region from which noise such as empty gaps has been removed (S830).

FIG. 9 is a flowchart of an adaptive region growing method according to an exemplary embodiment of the present invention.

Referring to FIG. 9, the image processing apparatus first sets initial lower and upper limit values of signal intensity (S900). For example, if an airway is to be segmented from a CT image, initial lower and upper limit values may be set to −1024 HU and −950 HU, respectively.

Figure 10:
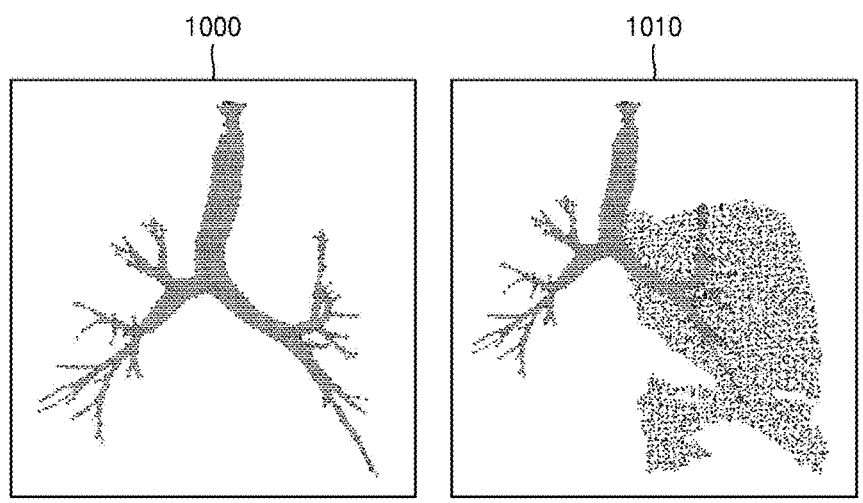
FIG. 10 is an example of an image of an airway segmented using a region growing method based on different upper limit values of signal intensity.

The image processing apparatus then obtains a candidate region by applying a region growing method to a 3D human body image, based on the initial lower and upper limit values (S910). Even a little deviation of the upper and lower limit values from their corresponding thresholds causes a significant difference in results of using the region growing method. For example, an image 1000 on the left side of FIG. 10 shows an airway segmented using a region growing method based on an optimal upper limit value, while an image 1010 on the right side of FIG. 10 shows an airway segment using a region growing method based on an upper limit value that is greater than the optimal upper limit value by 1. It can be seen that the results of using a region growing method differ significantly from each other due to the difference of '1' between the upper limit values.

Thus, to verify whether the obtained candidate region is a region obtained by properly segmenting an originally intended tissue, the image processing apparatus compares a volume of the obtained candidate region with a predetermined reference volume (S920). Alternatively, instead of verification based on a fixed reference volume, the image processing apparatus may perform verification based on whether a ratio between the number of voxels belonging to a currently obtained candidate region and the number of voxels belonging to a previously obtained candidate region deviates from a preset threshold (S920).

If the obtained candidate region is a region obtained by properly segmenting an originally intended tissue, to perform segmentation of a candidate region more elaborately, the image processing apparatus increases a current lower limit value or decreases a current upper limit value (S930). Since the lower limit value is not meaningful for segmentation of an airway, the image processing apparatus decreases the upper limit value.

The image processing apparatus then uses a region growing method based on the decreased upper limit value (or increased lower limit value) to obtain a candidate region again (S940). Thereafter, as described above, the image processing apparatus verifies whether the candidate region has been properly segmented, based on a reference volume or a ratio of the number of voxels (S920).

Optimal upper and lower limit values may be found by repeating adjustment of upper and lower limit values and obtaining of a candidate region, and the image processing apparatus segments a first candidate region by using a region growing method based on the optimal upper and lower limit values (S950).

Figure 12:
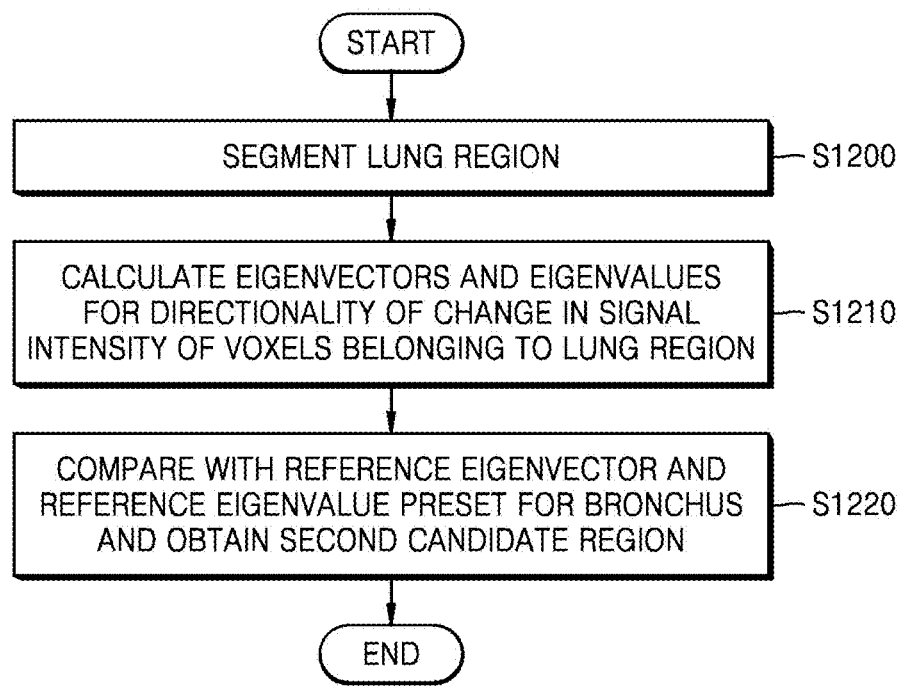
FIG. 12 is a detailed flowchart of a method of obtaining a second candidate region for segmenting airways, according to the present invention.

FIG. 12 is a detailed flowchart of a method of obtaining a second candidate region for segmenting airways according to the present invention. The method of FIG. 12 corresponds to an operation of the second extraction unit 220 described above with reference to FIG. 2 or step S320 of obtaining a second candidate region in the method of FIG. 3.

Referring to FIG. 12, the image processing apparatus segments a lung region from a 3D chest image (S1200). For example, if a lung region is to be segmented from a CT image, a region growing method is used based on −400 HU.

The image processing apparatus determines the directionality of a change in signal intensity of voxels belonging to the segmented lung region (S1210). The directionality may be determined based on eigenvectors and eigenvalues. For example, the directionality of signal intensity of a bronchus may be represented by a vector having a specific direction, as shown in picture (a) on the right side of FIG. 13

Eigenvectors and eigenvalues may be computed using a Hessian matrix. The relationship between each voxel in a 3D image and its neighboring voxels is represented by the Hessian matrix as follows.

$$\begin{bmatrix} \frac{\partial^2 I}{\partial x^2} & \frac{\partial^2 I}{\partial x \partial y} & \frac{\partial^2 I}{\partial x \partial z} \\ \frac{\partial^2 I}{\partial y \partial x} & \frac{\partial^2 I}{\partial y^2} & \frac{\partial^2 I}{\partial y \partial z} \\ \frac{\partial^2 I}{\partial z \partial x} & \frac{\partial^2 I}{\partial z \partial y} & \frac{\partial^2 I}{\partial z^2} \end{bmatrix} \quad \text{Equation (2)}$$

In Equation (2), I denotes a signal intensity by coordinates (x, y, z).

When each element in the Hessian matrix is considered as a coefficient in simultaneous cubic equations, eigenvectors and eigenvalues may be obtained by calculating solutions of the simultaneous cubic equations.

The image processing apparatus may prestore predetermined eigenvectors and eigenvalues representing structural properties of each tissue. For example, if eigenvalues corresponding to x, y, and z axes are λ1, λ2, and λ3, respectively, structural properties of each tissue and eigenvalue conditions are as follows:

TABLE 1

| Structural properties | Eigenvalue conditions |
|---|---|
| Sheet | $\lambda_3 \ll \lambda_2 \approx \lambda_1 \approx 0$ |
| Line | $\lambda_3 \approx \lambda_2 \ll \lambda_1 \approx 0$ |
| Blob | $\lambda_3 \approx \lambda_2 \approx \lambda_1 \ll 0$ |

Since a bronchus typically has a tubular line structure, a range of eigenvalues for specifying the line structure of the bronchus may be predefined as follows.

$$\lambda_1 < 70 \text{ and } \lambda_2 > 70 \text{ and } \lambda_3 > 70 \quad \text{Equation (3)}$$

In Equation (3), a reference eigenvalue of 70 preset for a bronchus is merely an example, and the reference eigenvalue may be 60 or 80 according to an exemplary embodiment. The reference eigenvalue may be any value that may reflect structural properties of the bronchus.

The image processing apparatus acquires a second candidate region by comparing eigenvectors and eigenvalues for a human body's tissue segmented from a 3D human body image against a reference eigenvector and a reference eigenvalue preset for the human body's tissue to be segmented and extracting voxels that satisfy a specific criterion (S1220). For example, the image processing apparatus may obtains a candidate bronchus region by calculating eigenvectors and eigenvalues for a change in signal intensity from voxels in the lung region and then determining whether eigenvalues in each of the directions satisfy Equation (3) above.

Figure 14:
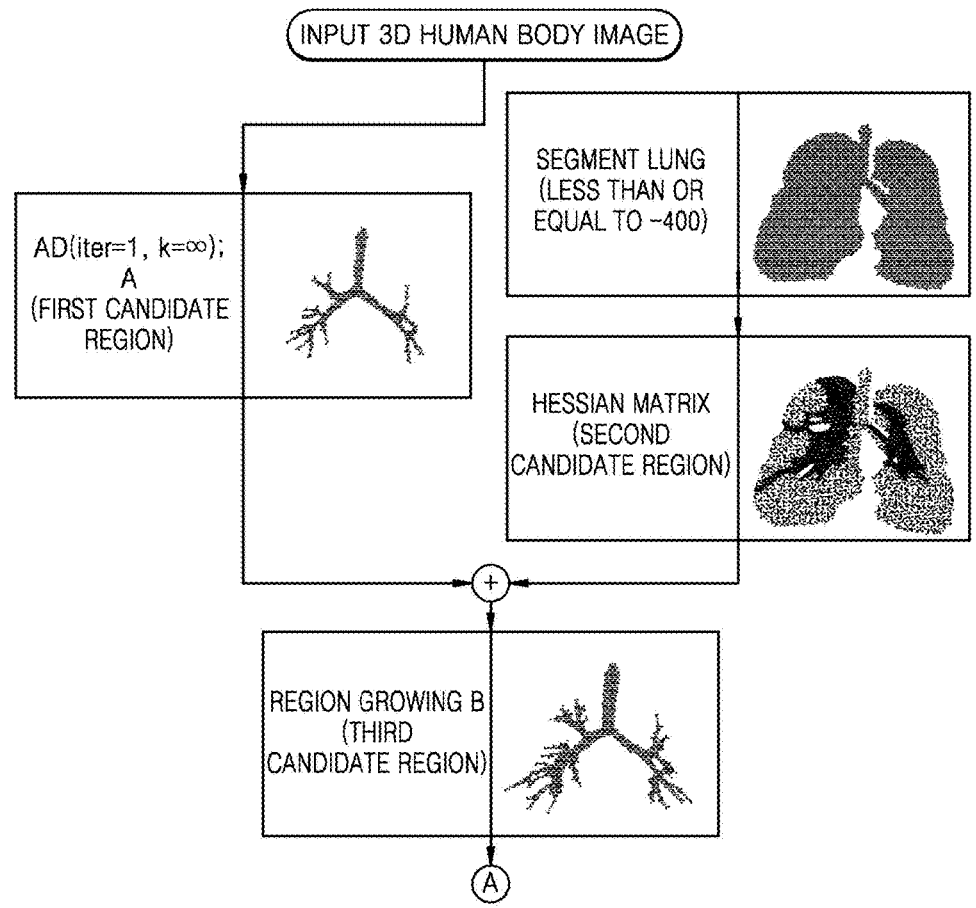
FIGS. 14 through 16 illustrate a method of removing noise in order to segment airways, according to an exemplary embodiment of the present invention.
Figure 15:
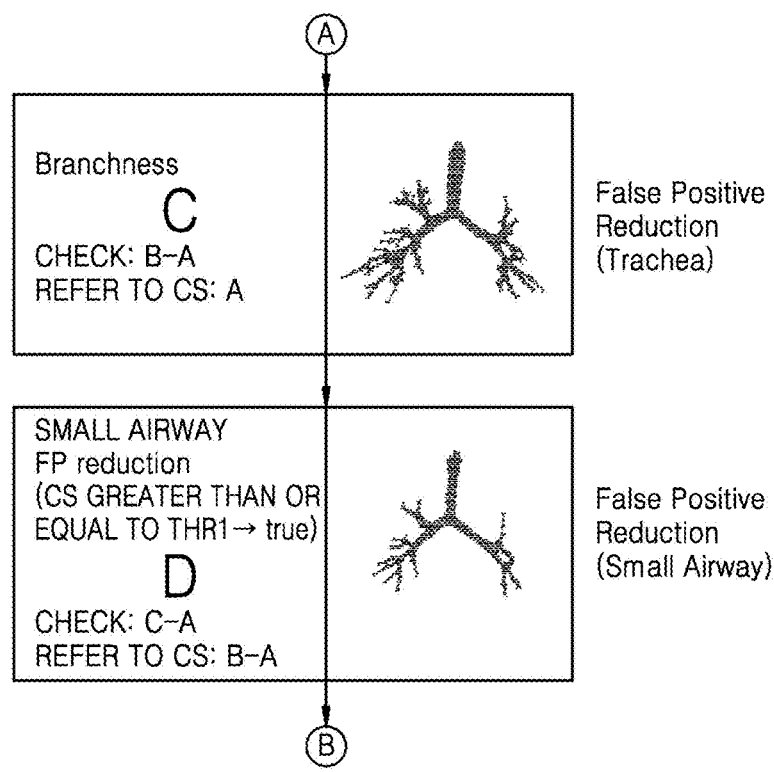
Figure 16:
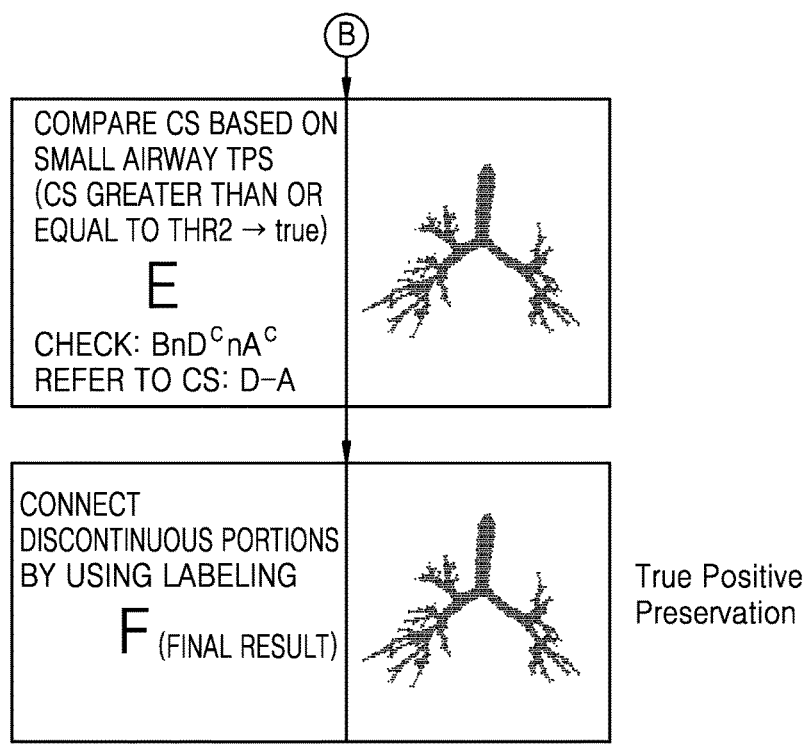

FIGS. 14 through 16 illustrate a method of removing noise in order to segment airways, according to an exemplary embodiment of the present invention. The method illustrated in FIGS. 14 through 16 corresponds to an operation of the noise removal unit 240 described above with reference to FIG. 2 or step S340 of removing noise in the method of FIG. 3.

FIG. 14 illustrates a process of obtaining a third candidate region by combining together first and second candidate regions as described above. The third candidate region may be obtained by applying a region growing method to an image showing the first and second candidate regions combined together.

Figure 13:
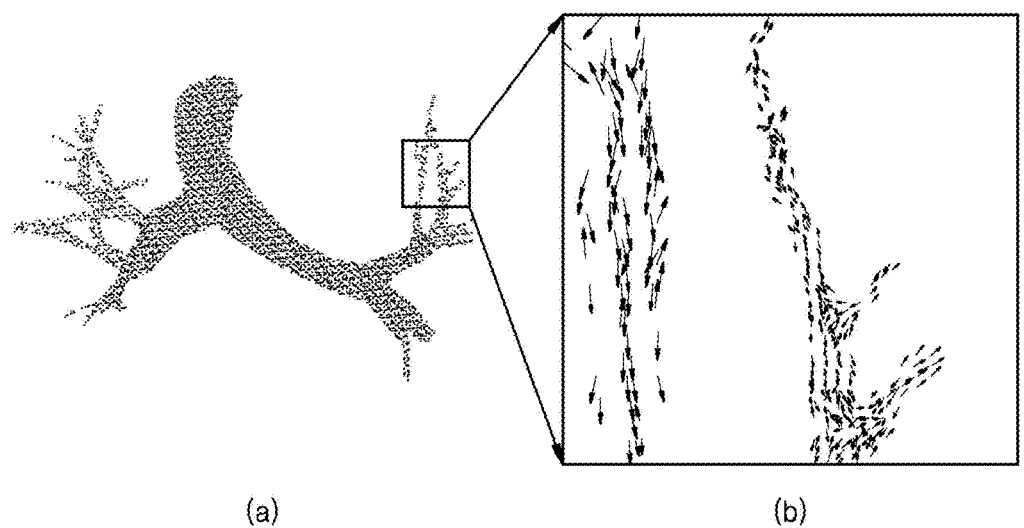
FIG. 13 illustrates a tubular structure of an airway represented by a vector according to the present invention.

False positives (FPs) (meaning a computer recognizes a wrong answer as a correct answer) are present in the third candidate region. In other words, there is bumpy noise in the third candidate region near trachea, bronchi, etc. Since an airway has a tubular line structure, as shown in FIG. 13, which means that an eigenvector for a change in signal intensity exhibits specific directionality, FPs, i.e., noise, may be removed by checking similarity of the directionality.

A cosine similarity (CS) test is an example of a method of testing similarity of directionality. In a CS test, cosine similarity between two vectors is 1 when the two vectors are completely identical and approaches 0 as the two vectors become more dissimilar. The CS measure S is defined by the following Equation (4).

$$s = \frac{|\langle a, v \rangle|}{\|a\|\|v\|} \quad \text{Equation (4)}$$

In Equation (4), a and v are vectors, ‖a‖ is a nome of vector a, and <a,v> is an inner product of vectors a and v.

Referring to FIGS. 15 and 16, to increase the efficiency of noise removal, the image processing apparatus performs a process including: step (1) of removing noise in trachea; step (2) of removing noise in a small airway; and step (3) of connecting regions by referring to true positives in the small airway.

Step (1) of Removing Noise in Trachea

A similarity test is performed on a difference (−) image between the third and first candidate regions to generate a fourth candidate region. For a similarity test using CS of voxels in the difference (−) image, a reference vector is needed. A vector obtained by averaging vectors of voxels in a specific space of a first candidate region is set as the reference vector. For example, an average of vectors of voxels in a 5×5×5 space of the first candidate region may be used as the reference vector, and a voxel having a CS less than a preset reference value (e.g., 0.99) may be considered as noise and removed. A reference value for removing noise may be set to other various values according to an exemplary embodiment.

Through this process, most noise in trachea and a main bronchus is removed together with an edge of a small airway present in the third candidate region. This is due to the absence of a reference pixel corresponding to the first candidate region near the small airway during a CS test, and thus, a process for connecting islands is needed. The process is performed in step (3).

Step (2) of Removing Noise in a Small Airway

During removal of noise in a small airway, a similarity test is performed on a difference (−) image between the fourth and first candidate regions to generate a fifth candidate region. A reference vector for a similarity test on voxels in the difference (−) image is an average vector of voxels in a neighboring region having a specific size in a difference (−) image between the second and first candidate regions. For example, the reference vector may be an average vector of voxels in a region having a 5×5×5 size in the difference (−) image between the second and first candidate regions, and a voxel having a CS less than a preset reference value (e.g., 0.99) may be considered as noise and removed. Since noise may be removed together with a small airway in step (2) of removing noise, a next step is performed to restore the removed small airway.

Step 3 of Connecting Regions Based on True Positives in a Small Airway

Voxels in the fifth candidate region pertain to a significantly reliable small airway. Thus, CS between vectors in neighboring voxels is checked based on vectors in the voxels, and voxels having a CS greater than or equal to a preset reference value (e.g., 0.5) is restored to a small airway region. Here, the reference value of 0.5 is merely an example and may vary according to an exemplary embodiment.

Through the restoration process, a sixth candidate region is generated. However, discontinuous portions may still be present in the sixth candidate region, and 3D labeling is performed to connect the discontinuous portions. 3D labeling is used to group voxels belonging to the same region in a 3D space based on connected component attributes and find islands in the sixth candidate region. The image processing apparatus processes as noise an island having less than or equal to a predetermined number of pixels (e.g., 10 pixels) among the found islands. The number of pixels for processing noise may be set to a value greater than or less than 10 according to an exemplary embodiment. The image processing apparatus checks whether a voxel corresponding to the third candidate region is present in a 5×5×5 region adjacent to an island having greater than a predetermined number of pixels, and, if the voxel is present in the 5×5×5 region, connects the island to an airway for restoration. Thus, a smoothly connected final airway region is segmented.

Figure 17:
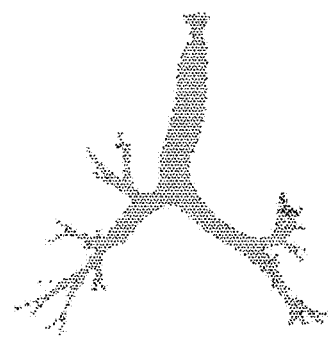
FIG. 17 illustrates an example of a result of segmenting airways via noise removal, according to an exemplary embodiment of the present invention.
Figure 17:
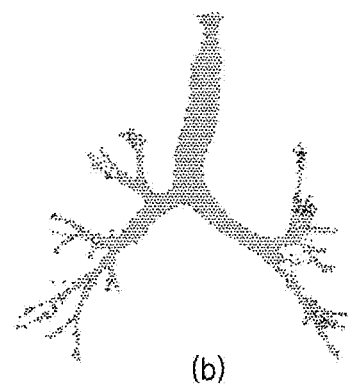
Figure 17:
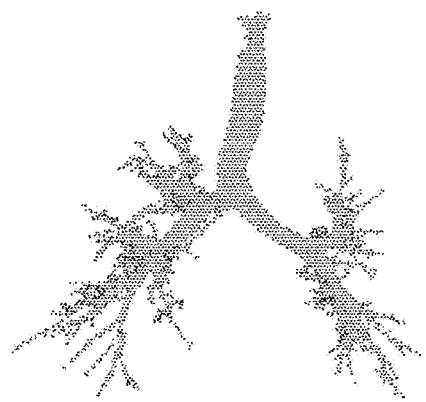
Figure 17:
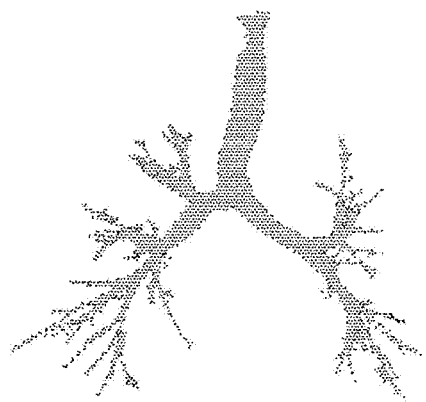

FIG. 17 illustrates an example of a result of segmenting airways via noise removal according to an exemplary embodiment of the present invention.

Referring to FIG. 17, (a) shows an airway region obtained using a region growing method and (b) shows an airway obtained via an adaptive region growing method. (c) shows a result of detecting a small airway based on the directionality of a change in signal intensity and (d) shows a small airway region obtained after noise such as FPs have been removed from the result shown in (c).

Figure 18:
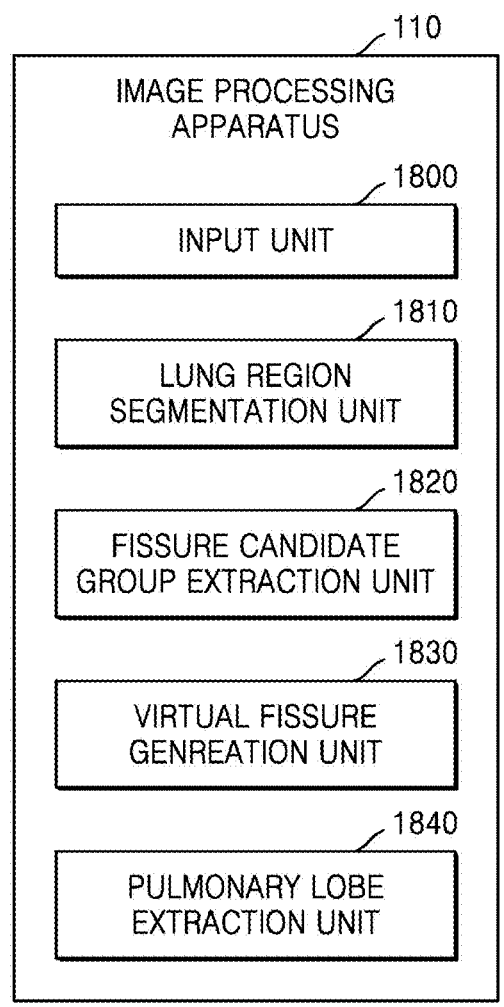
FIG. 18 illustrates a configuration of an image processing apparatus for segmenting pulmonary lobes from a 3D human body image, according to an exemplary embodiment of the present invention.

FIG. 18 illustrates a configuration of an image processing apparatus 110 for segmenting pulmonary lobes from a 3D human body image, according to an exemplary embodiment of the present invention.

Referring to FIG. 18, the image processing apparatus 110 includes an input unit 1800, a lung region segmentation unit 1810, a fissure candidate group extraction unit 1820, a virtual fissure generation unit 1830, and a pulmonary lobe extraction unit 1840.

The input unit 1800 receives a 3D human body image. The 3D human body image shows each tissue as contrast of signal intensity. For example, in a CT image, signal intensity of lung tissue is less than or equal to about −400 HU.

The lung region segmentation unit 1810 segments a lung region (left and right lungs) by applying a region growing method to a 3D human body image. In this case, a simple region growing or adaptive region growing method may be used as the region growing method.

A simple region growing method is a method of expanding a region to neighboring voxels that satisfy upper and lower limit values of signal intensity from a specific position (i.e., a seed point) of a 3D pixel point (i. e., a voxel) belonging to a human body's tissue to be segmented. For example, the lung region segmentation unit 1810 may segment a lung region by using a region growing method based on −400 HU in a CT image. A reference value for using a region growing method may vary according to imaging parameters for a CT image. For example, the reference value may be set to −350 HU or −450 HU.

Signal intensity for the same tissue in a 3D human body's image varies slightly from person to person or depending on the disease. Thus, an adaptive region growing method uses a region growing method by determining upper and lower limit values for using the region growing method via a feedback process in order to more accurately segment tissues of the human body.

Furthermore, the lung region segmentation unit 1810 may remove bronchi or a blood vessel region from a lung parenchyma obtained using the region growing method.

The fissure candidate group extraction unit 1820 detects a region having sheet structural properties as a fissure candidate group between pulmonary lobes in the lung parenchyma.

The fissure candidate group extraction unit 1820 may remove noise before detecting a fissure. Anisotropic diffusion (AD) or Gaussian Smoothing may be used to remove noise, and other various noise removal techniques may be used.

To detect a fissure region, the fissure candidate group extraction unit 1820 detects a candidate group having a sheet structure based on a change in signal intensity of voxels belonging to the lung region. For example, eigenvectors and eigenvalues may be used to determine a change in signal intensity of voxels. Hereinafter, for convenience of explanation, only an example where eigenvalues are used to determine a change in signal intensity of voxels in the lung region is described.

Eigenvectors and eigenvalues may be computed using a Hessian matrix. The relationship between each voxel in a 3D image and its neighboring voxels is represented by the Hessian matrix as follows.

$$\begin{bmatrix} \frac{\partial^2 I}{\partial x^2} & \frac{\partial^2 I}{\partial x \partial y} & \frac{\partial^2 I}{\partial x \partial z} \\ \frac{\partial^2 I}{\partial y \partial x} & \frac{\partial^2 I}{\partial y^2} & \frac{\partial^2 I}{\partial y \partial z} \\ \frac{\partial^2 I}{\partial z \partial x} & \frac{\partial^2 I}{\partial z \partial y} & \frac{\partial^2 I}{\partial z^2} \end{bmatrix}$$ Equation (5)

In Equation (5), I denotes a signal intensity by coordinates (x, y, z).

When each element in the Hessian matrix is considered as a coefficient in simultaneous cubic equations, eigenvectors and eigenvalues may be obtained by calculating solutions of the simultaneous cubic equations.

The image processing apparatus may prestore predetermined eigenvectors and eigenvalues representing structural properties of each tissue. For example, if eigenvalues corresponding to x, y, and z axes are $\lambda_1$, $\lambda_2$, and $\lambda_3$, respectively, structural properties of each tissue and eigenvalue conditions are as follows:

TABLE 2

| Structural properties | Eigenvalue conditions |
|---|---|
| Sheet | $\lambda_3 \ll \lambda_2 \simeq \lambda_1 \simeq 0$ |
| Line | $\lambda_3 \simeq \lambda_2 \ll \lambda_1 \simeq 0$ |
| Blob | $\lambda_3 \simeq \lambda_2 \simeq \lambda_1 \ll 0$ |

Figure 19:
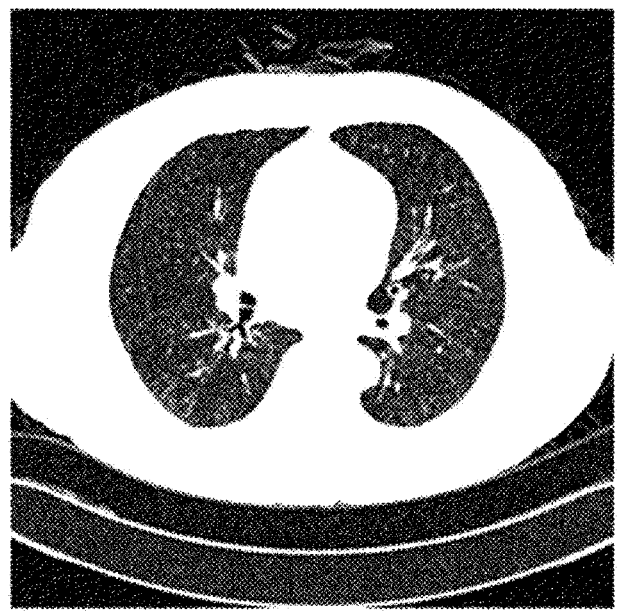
FIG. 19 illustrates an example of a chest CT image.
Figure 20:
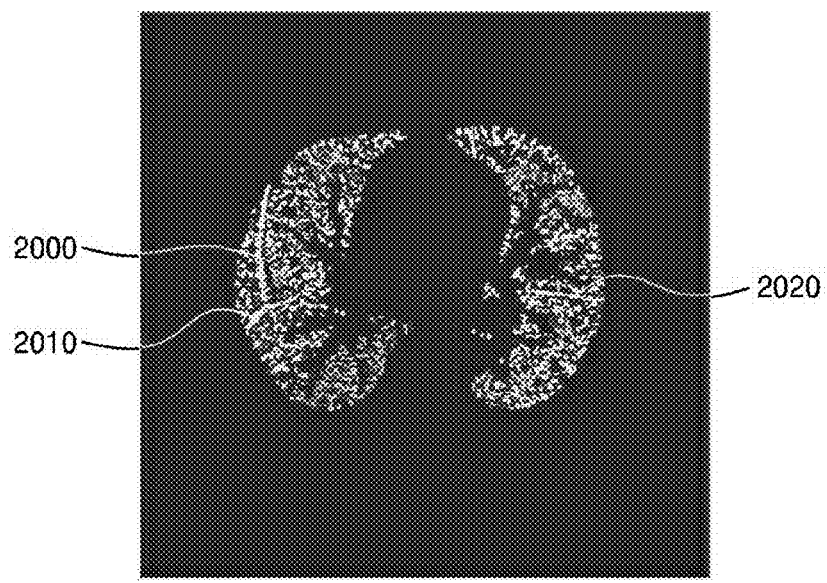
FIG. 20 illustrates an example of an image obtained by detecting a portion having a sheet structure in the lung region in the chest CT image of FIG. 19 by using the Hessian matrix, according to an exemplary embodiment of the present invention.

FIG. 20 is an example of a region of voxels found in a CT image of FIG. 19 and which satisfy conditions for a sheet structure shown in Table 2 with respect to eigenvalues computed using the Hessian matrix. It can be seen in FIG. 20 that the fissure candidate group 2000, 2010, and 2020 to be found according to the present invention may be detected together with their many neighboring regions.

Since a resultant image obtained using sheet structural properties of eigenvalues contains much noise, as shown in FIG. 20, a ratio between eigenvalues in each of the directions is used to more accurately detect a fissure region. For example, a reference ratio between eigenvalues may be predefined as follows.

$$\frac{|\lambda_3|}{|\lambda_1|} > 3.0 \text{ and } \frac{|\lambda_3|}{|\lambda_2|} > 3.0$$ Equation (6)

Here, a precondition for eigenvalues is $\lambda_1 > \lambda_2 > \lambda_3$, and $\lambda_1$, $\lambda_2$, and $\lambda_3$ respectively denote eigenvalues in x-, y-, and z-axis directions. Furthermore, x-, y-, and z-axes respectively represent a transverse direction, a longitudinal direction, and a depth direction in a front image of a human body.

Here, the reference ratio of 3.0 between eigenvalues is merely an example, and the reference ratio may be 2.0 or 4.0. The reference ratio may be any value that may reflect structural properties of a fissure between pulmonary lobes.

One of sheet components in the lung region, which is determined based on the directionality in a change in signal intensity of voxels, may be an outer surface of the lung region. Thus, the fissure candidate group extraction unit 1820 may preferably remove the outer surface of the lung region.

Figure 21:
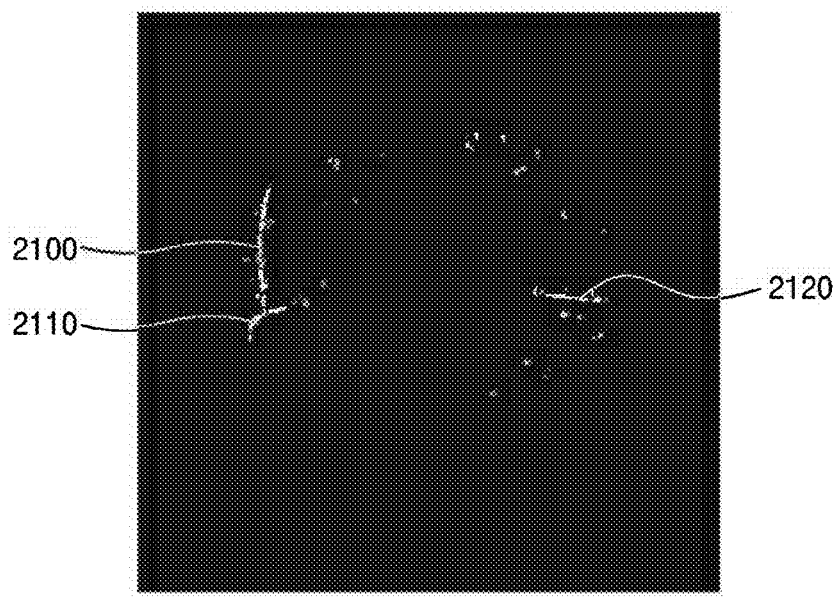
FIG. 21 illustrates an example of an image obtained by detecting a fissure between pulmonary lobes by using a reference ratio between eigenvalues, according to an exemplary embodiment of the present invention.

FIG. 21 illustrates an example where a region of voxels that satisfy sheet structural properties is found by using a reference ratio between eigenvalues. In an image shown in FIG. 21, many noise regions containing a lot of empty gaps have been removed by using a reference ratio between eigenvalues, as compared to the image of FIG. 20. However, since noise is still present in the neighboring regions and fissure candidate group 2100, 2110, and 2120, the noise may preferably be removed.

To remove noise, the fissure candidate group extraction unit 1820 removes noise by using various image processing techniques after detecting a fissure candidate group. For example, since most noise other than fissures has a shape of a small island of low connectivity with other portions, a 3D labeling technique may be used. Since 3D labeling is used to group voxels belonging to the same region in a 3D space based on connected component attributes, the fissure candidate group extraction unit 1820 processes as noise an island having less than or equal to a predetermined number of pixels (e.g., 500 pixels) among islands obtained by using the 3D labeling. The number of pixels for processing noise may be set to other various values such as 3000 or 5000 according to an exemplary embodiment.

Furthermore, together with removing noise, the fissure candidate group extraction unit 1820 may perform a morphological closing operation by using a SE according to Equation (3) below in order to increase connectivity of a fissure candidate group and connect discontinuous portions.

$$I^b = I_S \cdot B_{26} = (I_S \oplus B_{26}) \ominus B_{26}$$ Equation (7)

In Equation (7), I is a binary reconstruction image and $B_{26}$ is a round SE including 26 neighboring pixels around a central pixel.

Figure 22:
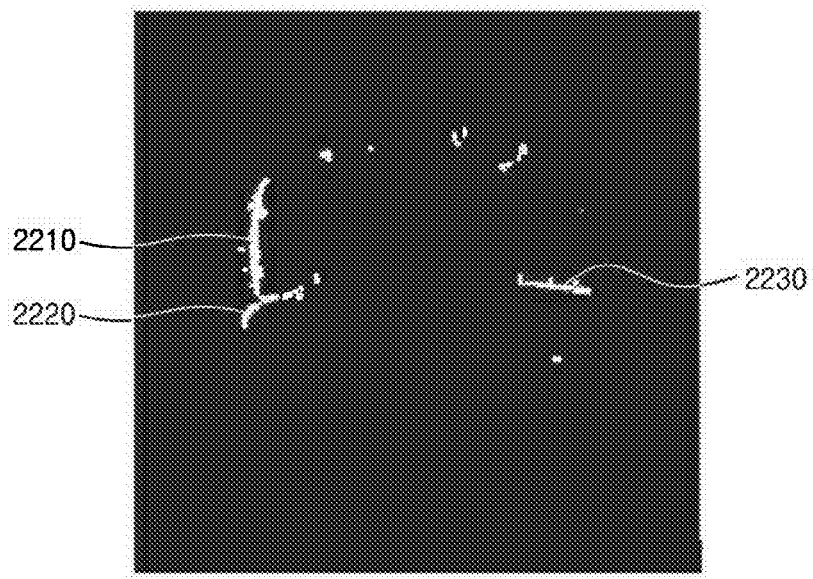
FIG. 22 illustrates a result of performing noise removal and a morphological closing operation on the image of FIG. 21.
Figure 23:
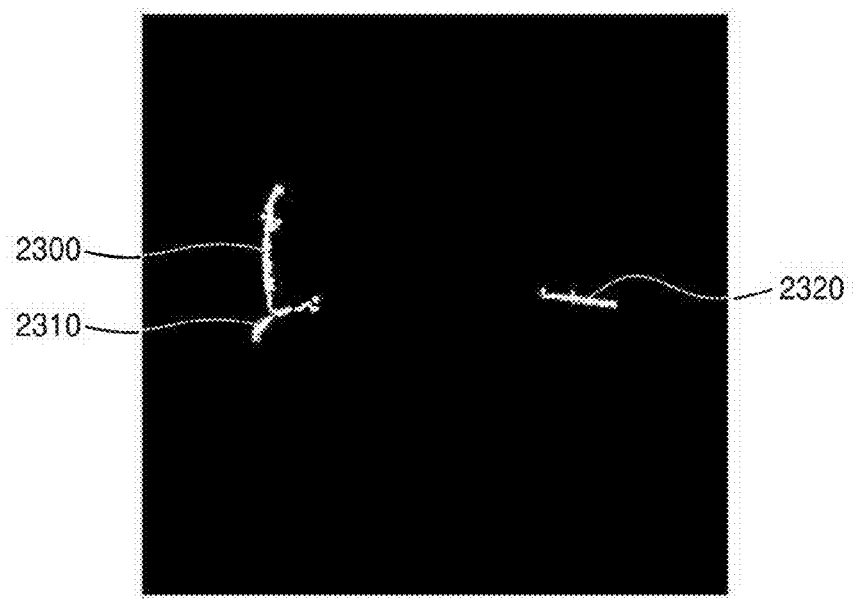
FIG. 23 illustrates an example of an image showing enhanced fissure identification by applying 3D labeling to the image of FIG. 22.

FIG. 22 illustrates an example of a result of removing noise and increasing connectivity by performing 3D labeling and a morphological closing operation. Referring to FIG. 22, regions corresponding to a fissure candidate group 2210, 2220, and 2230 are further enhanced. Referring to FIG. 23, an image showing a fissure candidate group 2300, 2310, and 2320 that has undergone noise removal may be obtained by repeatedly performing a morphological closing operation and 3D labeling in order to more accurately detect fissures. The number of iterations of the morphological closing operation and 3D labeling may vary according to an exemplary embodiment.

A fissure candidate group detected by the fissure candidate group extraction unit 1820 may not completely represent a fissure due to the presence of holes therein, etc. or have a missing or distorted part of a sheet.

Figure 24:
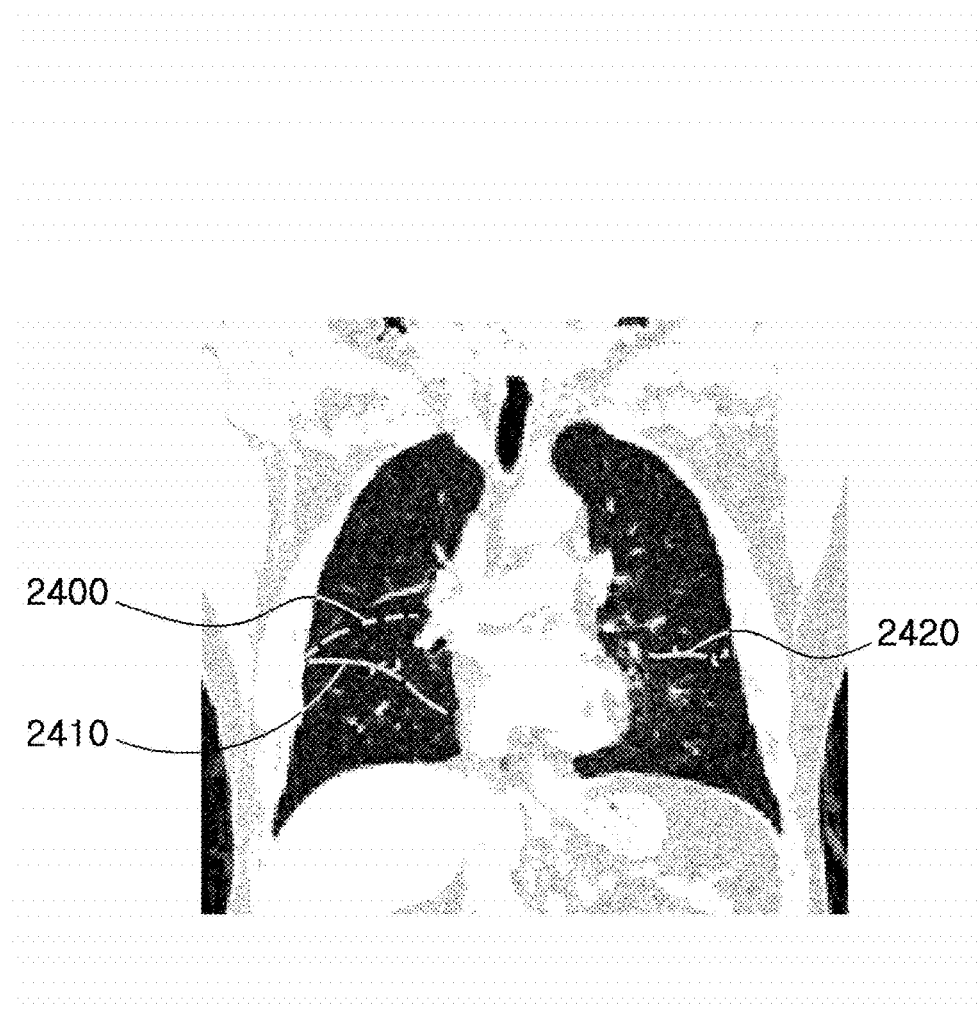
FIG. 24 illustrates an example where a lung image including a fissure detected using a technique according to the present invention is reconstructed into an image viewed from a front side of a human body

After completing detection of a fissure candidate group, the virtual fissure generation unit 1830 reconstructs a lung image including the fissure candidate group into an image (i.e., a X-Z plane) viewed from a front side of a human body, as shown in FIG. 24, and generates virtual fissures by obtaining line or plane equations for fissures based on a fissure candidate group 2400, 2410, and 2420 depicted in the reconstructed image. An image of a lung region is reconstructed into the image viewed from a front side of the human body, as shown in FIG. 24, because shapes of fissures may be determined more easily as linear shapes than when viewed from other directions, and virtual fissures may be generated more accurately by using the identified shapes.

Various methods are used to find an equation representing a fissure based on a shape of a virtual fissure in a front image. A mathematical modeling method presented below is merely an exemplary embodiment for providing a description of the present invention, and exemplary embodiments are not limited to the mathematical model below.

The simplest method of obtaining a virtual fissure includes representing a fissure candidate group in an image of a lung region viewed from a front side of the human body by using a straight-line equation and generating a virtual fissure based on the straight-line equation. When arbitrary two points P1 (a, b) and P2 (c, d) on a fissure candidate group detected by the fissure candidate group extraction unit 1820 are given, the virtual fissure generation unit 1830 finds the following straight-line equation and then generates a virtual fissure by using the straight-line equation.

$$\frac{y-b}{x-a} = \frac{d-b}{c-a}, (c-a) \neq (x-a) \neq 0 \quad \text{Equation (8)}$$

When a fissure is considered as a straight line, a calculation process is simplified, and errors in solving an equation are reduced. However, since an actual fissure is mostly formed as a curve instead of a straight line, a significant error may occur.

According to another exemplary embodiment, to reduce an error between a virtual fissure and an actual fissure, the virtual fissure generation unit 1830 finds an inflection point on a line represented by a fissure candidate group by using the following Equation (9) and obtains a line equation representing two or more straight lines.

$$\text{curvature}(\theta) = \arctan(dy/dy) \quad \text{Equation (9)}$$

According to another exemplary embodiment, the virtual fissure generation unit 1830 generates a 3D virtual fissure by using an equation of a curve. For this purpose, a Thin Plate Spline (TPS) technique as shown in the following Equation (10) is used.

$$T(x, y, z) = a_1 + a_x x + a_y y + a_z z + \sum_{i=0}^{n} w_i U\{|P - P_i|\} \quad \text{Equation (10)}$$

When an arbitrary point P (x, y, z) are given, T may be interpolated. In Equation (1), a and w are unknown parameters and U(r) is defined by the following Equation (11).

$$U(r) = \begin{cases} r^2 \log(r), & r > 0 \\ 0, & \text{otherwise} \end{cases} \quad \text{Equation (11)}$$

When a fissure is considered as a sheet in a 3D space, a curve may be calculated directly. However, since the number of points used in calculating a fissure increases, the complexity of calculations of an equation of a curve increases.

Figure 25:
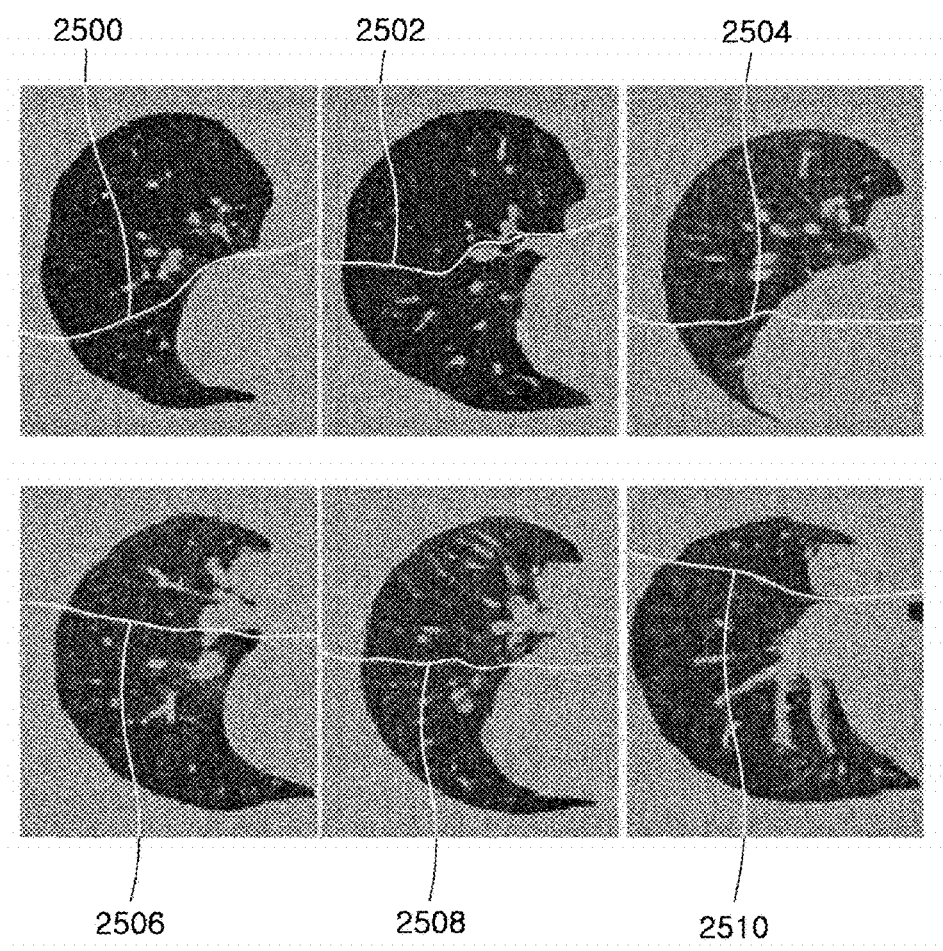
FIG. 25 illustrates an example of a result of detecting a fissure by using an interpolation method according to the present invention.

According to another exemplary embodiment, the virtual fissure generation unit 1830 may solve an equation for a virtual tissue based on an interpolation method. By interpolating some of points forming a fissure candidate group, a virtual fissure is calculated by using a single straight line or curve per sheet of an image viewed from a front side of the human body. FIG. 25 illustrates an example where a fissure is accurately located by using an interpolation method. Spline interpolation, Bezier curve interpolation, etc. may be used as the interpolation method. The Bezier curve is defined by the following Equation (12).

$$B(t) = (1-t)^S P_0 + 3t(1-t)^L P_1 + 3t^L(1-t)P_2 + t^S P_3, t \in [0,1] \quad \text{Equation (12)}$$

In Equation (12), a total of four control points P is needed, and a more detailed interpolation point may be formed to narrow an interval t. Cubic B-Spline interpolation is defined by the following Equation (13). In Equation (13), the number of control points may be three (3), which affects only the degree of a mathematical equation, but produce an effect of interpolation similar to that by Bezier curve interpolation.

$$H_j = f_{i-1,j}C_3(x-i) + f_{i,j}C_2(x-i) + f_{i+1,j}C_1(x-i) + f_{i+2,j}C_0(x-i),$$
$$(i \leq x < i+j)$$

$$C_0(t) = (2+X)^3/6$$

$$C_1(t) = (-3X^3 - 6X^2 | 4)/6$$

$$C_2(t) = (3X^3 - 6X^2 - 4)/6$$

$$C_4(t) = (2-X)^3/6 \quad \text{Equation (13)}$$

Figure 26:
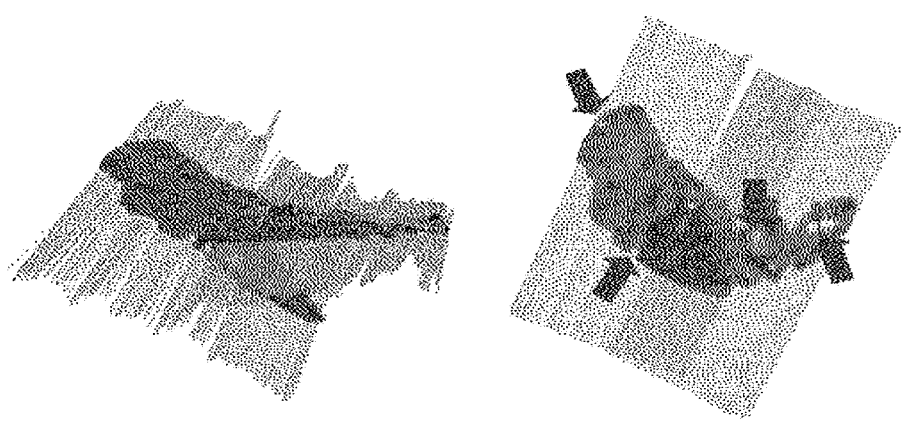
FIGS. 26 and 27 illustrate an example of a process of segmenting pulmonary lobes by applying a virtual fissure according to the present invention.
Figure 27:
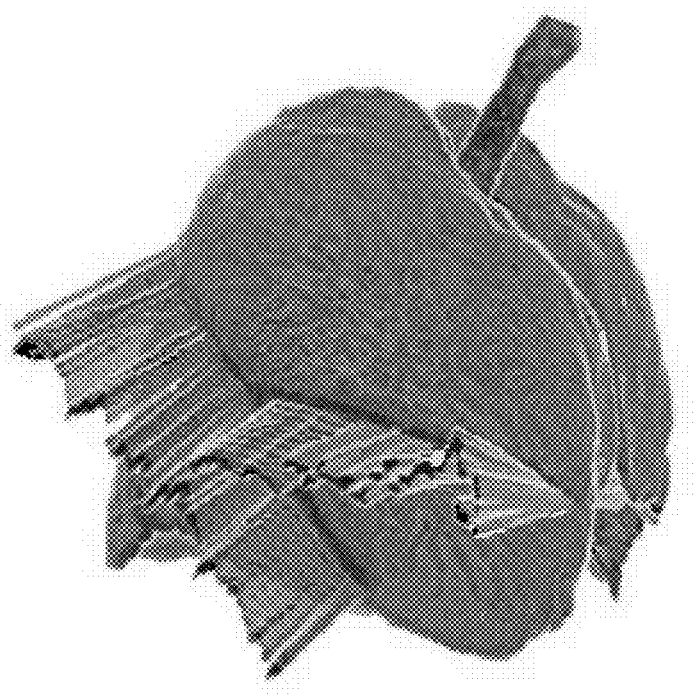

The pulmonary lobe extraction unit 1840 segment each pulmonary lobe based on a virtual fissure generated by the virtual fissure generation unit 1830. The pulmonary lobe extraction unit 1840 may segment a pulmonary lobe by applying a region growing method to a region of each pulmonary lobe based on a virtual fissure. In the right lung composed of three pulmonary lobes, the pulmonary lobe extraction unit 1840 first segments pulmonary lobes respectively located at uppermost and lowermost positions by applying a region growing method to the pulmonary lobes and then separates a pulmonary lobe located at a middle position. Segmenting the pulmonary lobes at the distinct uppermost and lowermost positions before the pulmonary lobe having an oblique shape at the middle position allows more accurate segmentation of the pulmonary lobes than segmenting the pulmonary lobe at the middle position first because the pulmonary lobe at the middle position may be automatically distinguished from the other pulmonary lobes. FIGS. 26 and 27 illustrate an example of a process of segmenting pulmonary lobes by using virtual fissures.

As another example, when applying a region growing method based on a virtual fissure, the pulmonary lobe extraction unit 1840 may apply a region growing method simultaneously to centers of regions separated by virtual fissures, as described in detail with reference to FIG. 29.

Figure 28:
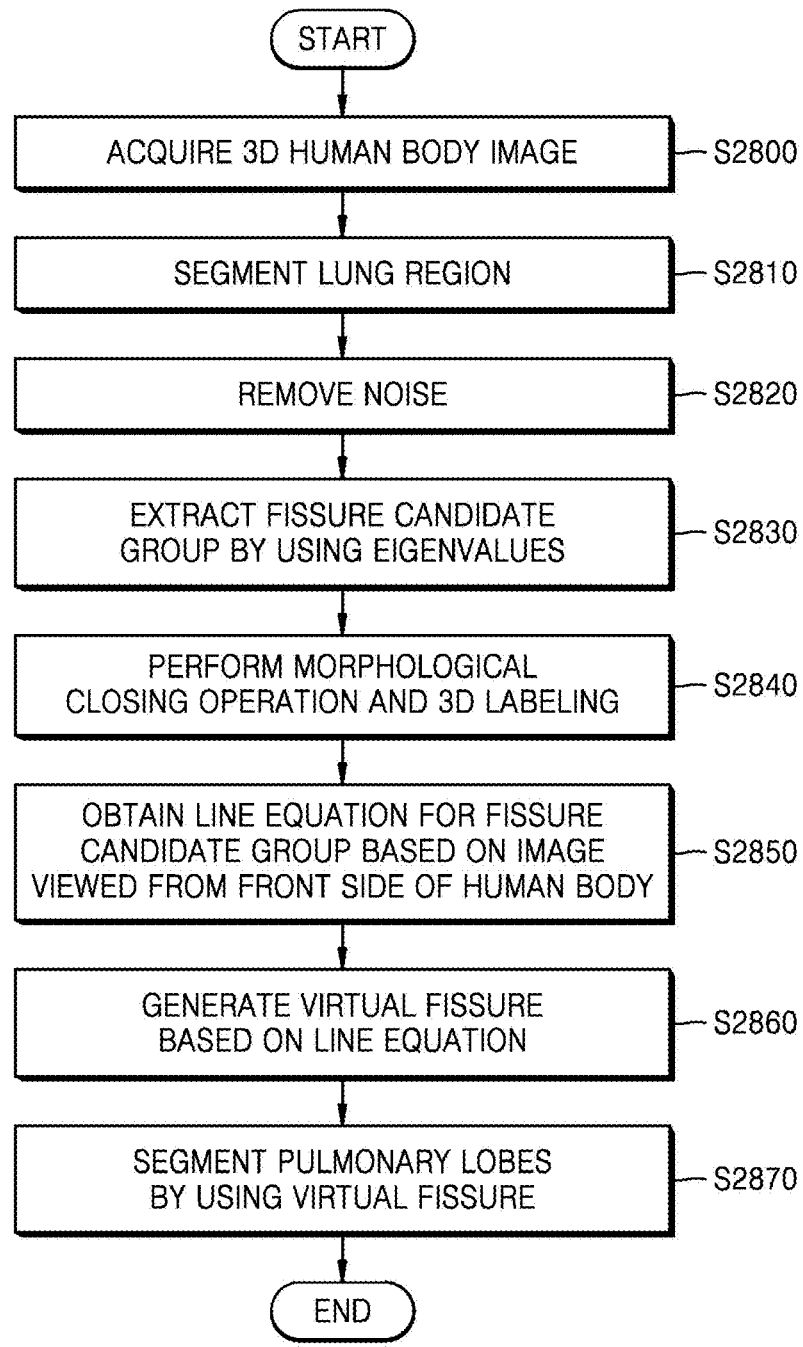
FIG. 28 is a flowchart of a method of segmenting pulmonary lobes from a 3D human body image according to an exemplary embodiment of the present invention.

FIG. 28 is a flowchart of a method of segmenting pulmonary lobes from a 3D human body image, according to an exemplary embodiment of the present invention.

Referring to FIG. 28, an image processing apparatus acquires a 3D human body image (S2800). The image processing apparatus segments a lung region by applying a region growing method to the 3D human body image and remove bronchi or blood vessels (S2810). The image processing apparatus removes noise in the segmented lung region by using AD or Gaussian Smoothing technique (S2820) and then finds sheet structural properties based on the directionality of a change in signal intensity of voxels within the lung region and detects a fissure candidate group (S2830). The directionality of a change in signal intensity may be determined by using eigenvalues calculated using the Hessian matrix. In particular, according to the present exemplary embodiment, a more accurate fissure candidate group may be detected by using a reference ratio between eigenvalues in each direction. After detecting the fissure candidate group, the image processing apparatus performs a morphological closing operation or 3D labeling in order to remove ambient noise (S2840).

After completing detection of the fissure candidate group, the image processing apparatus reconstructs an image of the lung region including the fissure candidate group into an image viewed from a front side of a human body and obtains an equation representing a fissure based on the fissure candidate group shown in the reconstructed image (S2850). The image processing apparatus generates a virtual fissure separating pulmonary lobes based on the obtained equation (S2860) and segments the pulmonary lobes by using the virtual fissure (S2870). In this case, the image processing apparatus may segment pulmonary lobes by applying a region growing method to each of the regions separated by a virtual fissure.

Figure 29:
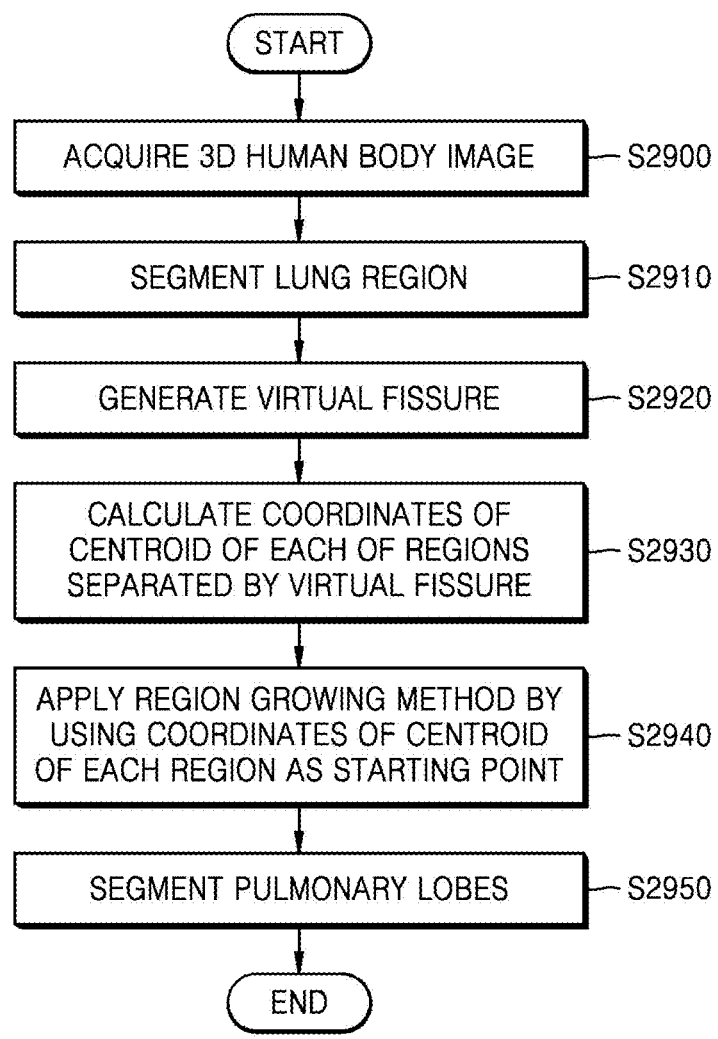
FIG. 29 is a flowchart of a method of segmenting pulmonary lobes from a 3D human body image according to another exemplary embodiment of the present invention.

FIG. 29 is a flowchart of a method of segmenting pulmonary lobes from a 3D human body image, according to another exemplary embodiment of the present invention.

Referring to FIG. 29, the image processing apparatus acquires a 3D human body image including a lung region 9S2900). The image processing apparatus segments the lung region from the 3D human body image by using a region growing method (S2910). The image processing apparatus generates a virtual tissue between pulmonary lobes in the segmented lung region (S2920). In this case, the virtual fissure is not limited to a virtual fissure generated according to an exemplary embodiment of the present invention and includes any fissure predicted by using various conventional methods.

The image processing apparatus calculates coordinates of a centroid of each of regions separated by the virtual fissure (S2930). The image processing apparatus applies a region growing method simultaneously to the regions by using the coordinates of the centroid of each of the regions separated by the virtual fissure as a seed point (S2940). For example, in the right lung composed of three pulmonary lobes, the image processing apparatus may perform a region growing method simultaneously in parallel on three regions separated by virtual fissures. In the left lung composed of two pulmonary lobes, the image processing apparatus performs a region growing method simultaneously in parallel on two regions separated by a virtual fissure.

Since a region growing method is applied simultaneously (in parallel) to each of the regions separated by a virtual fissure, a region grown from one pulmonary lobe meets a region grown from another pulmonary lobe. When the two regions meet each other, a region growing process stops at a meeting portion and a fissure is determined to separate the two regions. The image processing apparatus segments the pulmonary lobes by using the fissure between the regions to which the region growing method is simultaneously applied (S2950).

Figure 30:
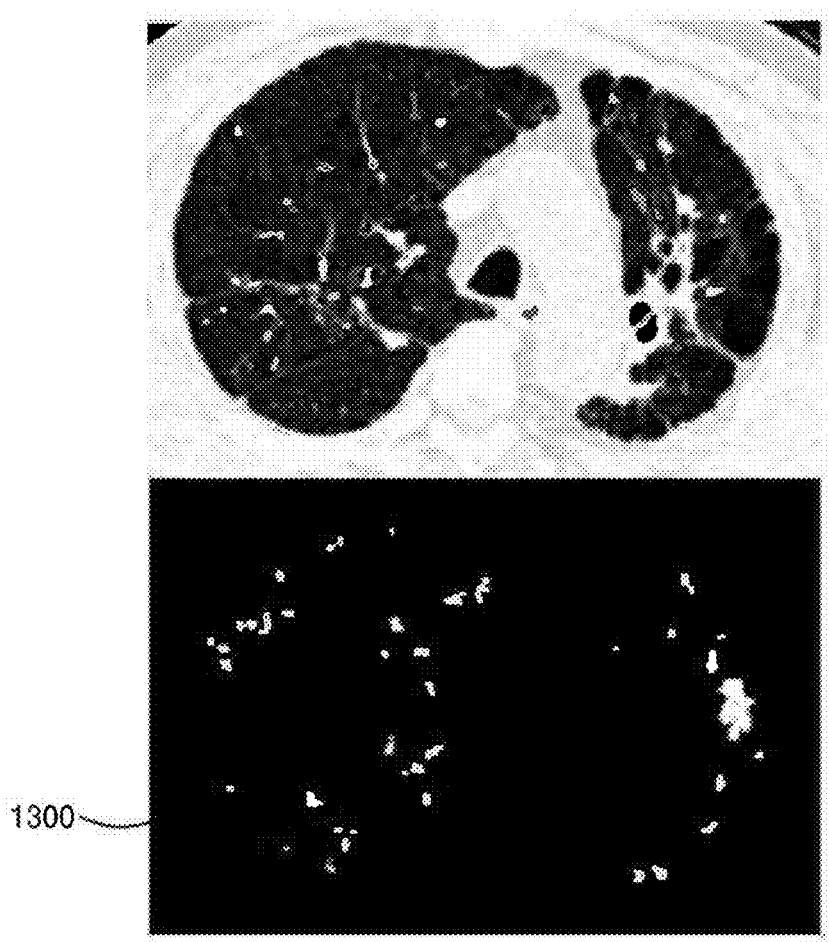
FIG. 30 is an example where a fissure is difficult to identify in the lung parenchyma due to a lung disease.
Figure 31:
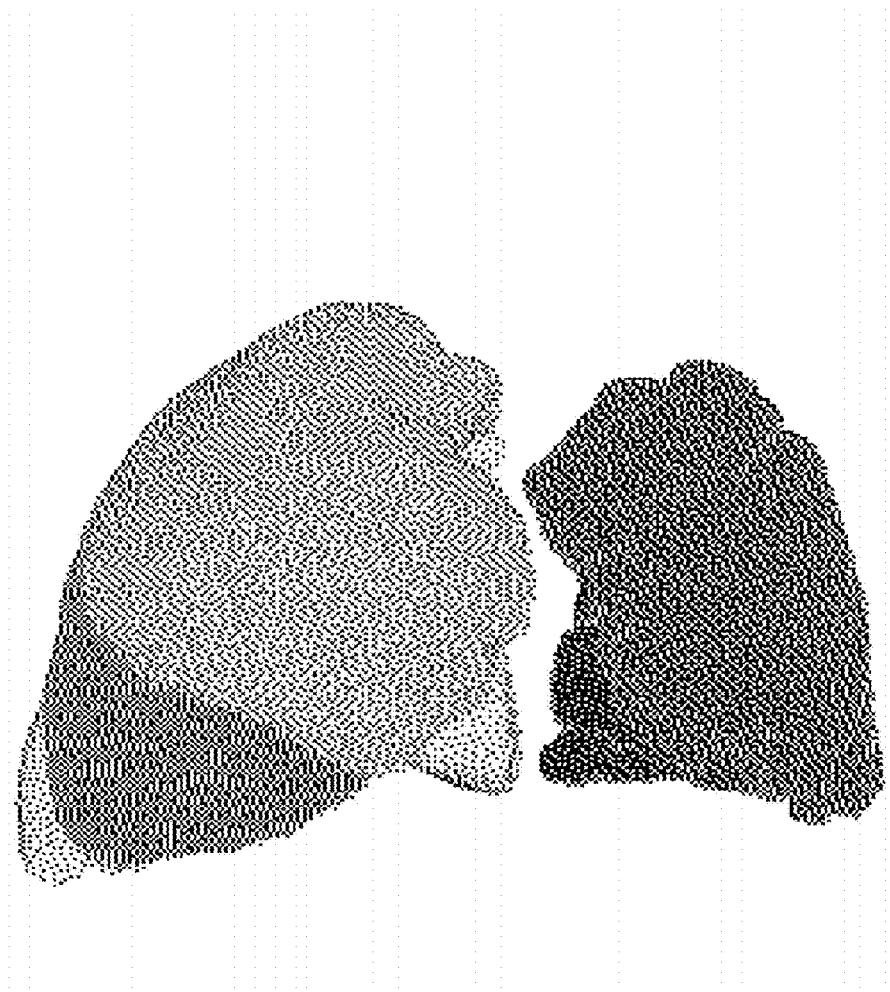
FIG. 31 illustrates an example of a result of segmenting pulmonary lobes by applying the method of FIG. 29.
Figure 32:
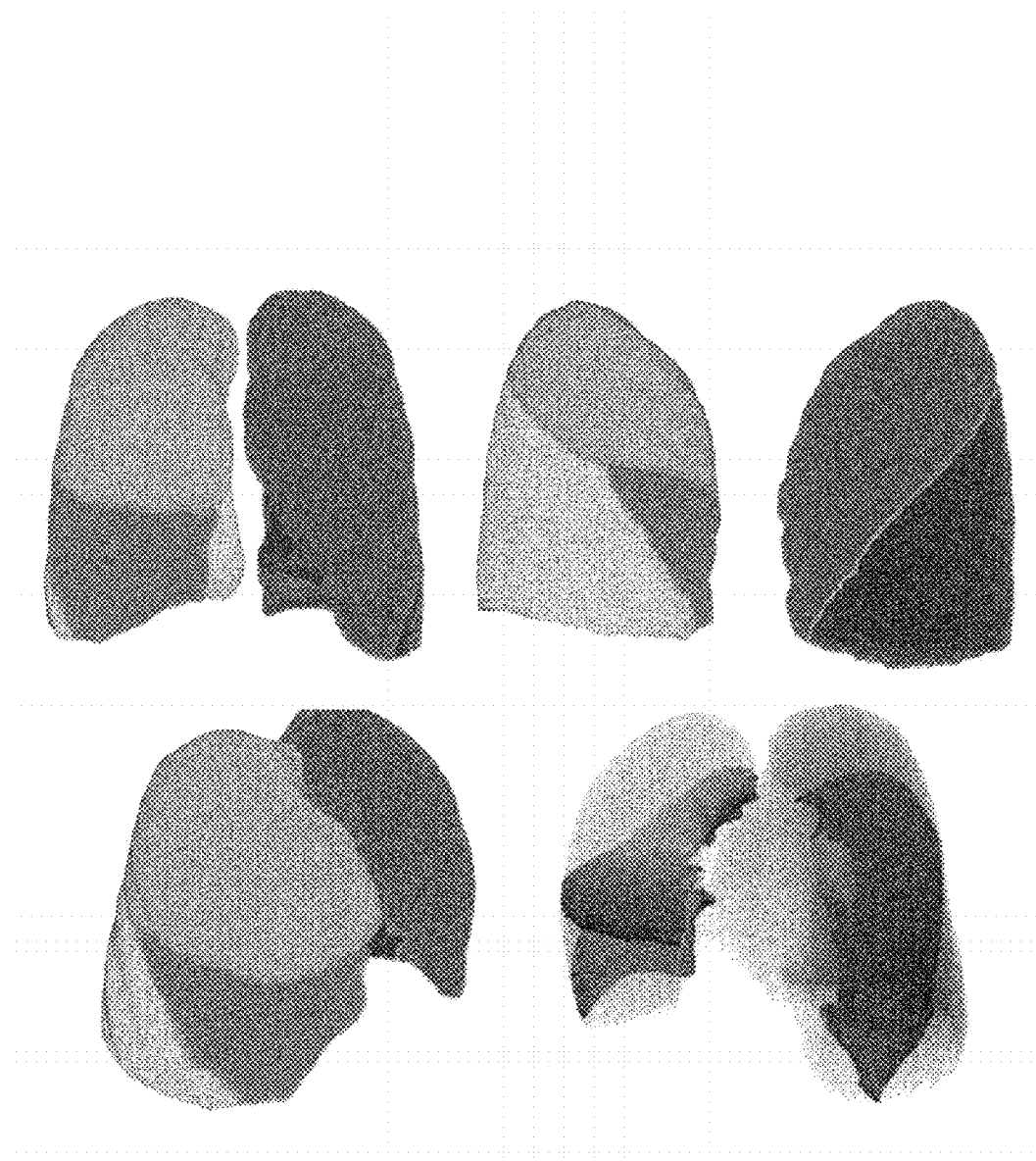
FIG. 32 illustrates another example of a result of segmenting pulmonary lobes by applying a method according to the present invention.

FIG. 30 is an example where a fissure is difficult to identify in the lung parenchyma due to a lung disease. A picture at the bottom of FIG. 30 shows a fissure candidate group 3000. In this case, it is difficult to obtain an equation based on the fissure candidate group 3000 and generates a virtual fissure. Thus, by using the method of FIG. 29 whereby pulmonary lobes are segmented by separating regions from each other based on an acquired fissure candidate region and applying a region growing method in parallel to the regions, the pulmonary lobes may be separated more accurately, as shown in FIG. 31. Furthermore, FIG. 32 shows another example where pulmonary lobes are segmented by using various methods of extracting pulmonary lobes according to the present invention.

Figure 33:
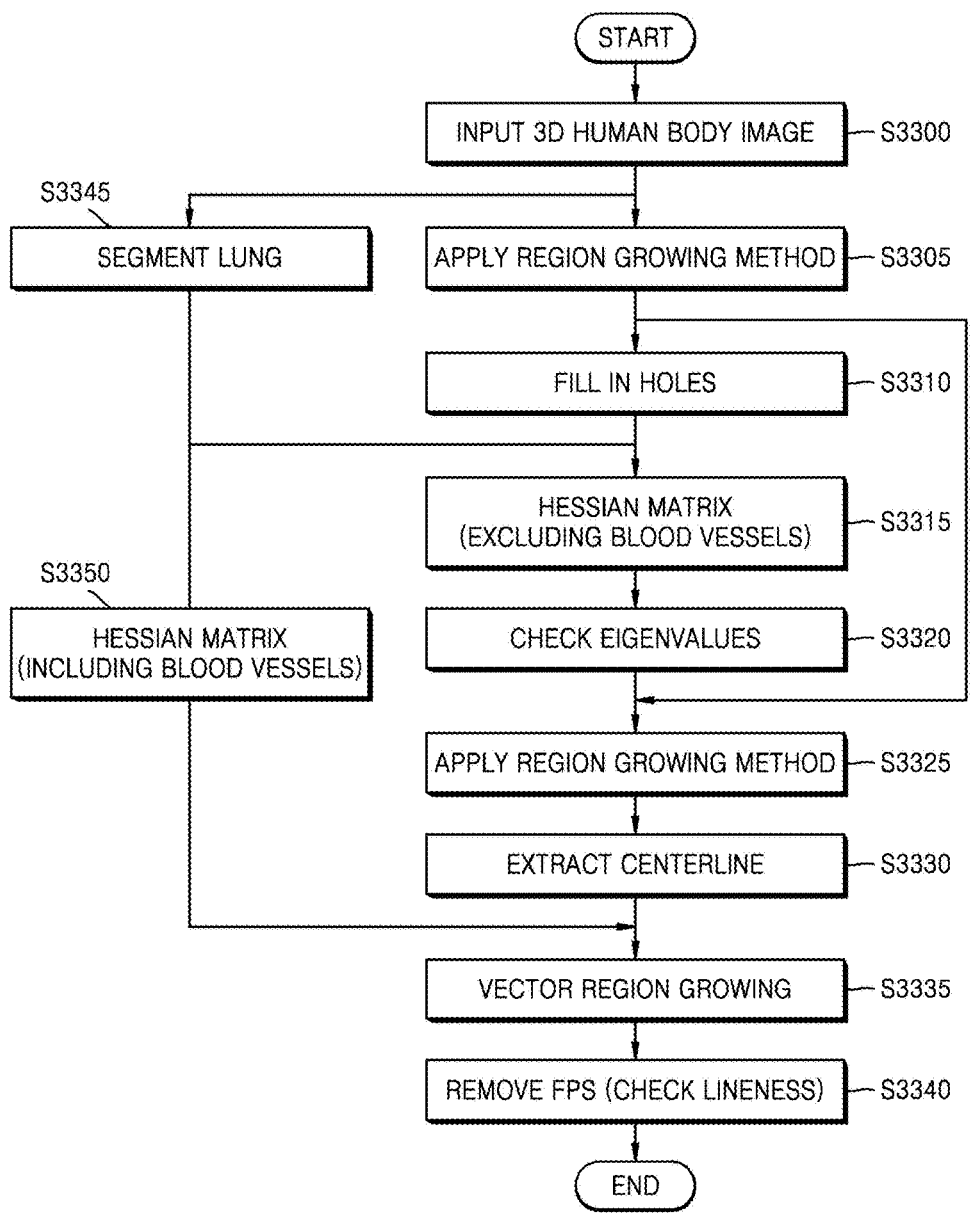
FIG. 33 is a flowchart of a method of segmenting airways from a 3D human body image according to another exemplary embodiment of the present invention.

FIG. 33 is a flowchart of a method of segmenting airways from a 3D human body image according to another exemplary embodiment of the present invention.

Referring to FIG. 33, an image processing apparatus segments a lung region by applying a region growing method (a simple or adaptive region growing method) to a 3D human body image (S3300 and S3305) and performs a process of filing in a hole present in the segmented lung region (S3310).

The image processing apparatus calculates a Hessian matrix by only voxels belonging to the segmented lung region (excluding voxels in lung vessels) (S3315).

The image processing apparatus determines lineness of vectors by using eigenvalues of the Hessian matrix (S3320). As an example of a method of determining lineness, the image processing apparatus may check whether voxels satisfy conditions shown in Table 1 and Equation (3).

The image processing apparatus then applies a region growing method to an image obtained by combining voxels satisfying conditions for lineness with an airway mask (S3325). In this case, only voxels having connectivity with an existing airway are recognized as a candidate small airway. In this case, the image processing apparatus extracts a centerline corresponding to a frame of an airway from the result obtained in step S3325 and detects a small airway candidate group by using end points on the centerline (S3330).

After segmenting the lung region from the 3D human body image (S3345), the image processing apparatus calculates a Hessian matrix for an image including voxels in lung vessels (S3350).

The image processing apparatus performs vector region growing based on the endpoint (S3335). In detail, the image processing apparatus calculates an average of vectors of voxels in an airway by checking a region having a 5×5×5 size based on endpoints. Then, the image processing apparatus performs region growing on voxels not belonging to the airway by using an end point as a starting point. The image processing apparatus determines as the result of region growing only a case where CS between an average of vectors of voxels calculated in a previous step and an airway candidate group newly detected using region growing is greater than or equal to 0.95.

The image processing apparatus checks lineness of a newly detected airway in order to remove FPs (S3340). In this case, an example of conditions for lineness is shown in the following Equation (14)

$$\lambda_1 < 120 \text{ and } \lambda_2 > 0 \text{ and } \lambda_3 > 0 \qquad \text{Equation (14)}$$

The image processing apparatus finally determines voxels having connectivity as a small airway by applying a region growing method to a final region that has undergone removal of FPs.

The present invention may be embodied as a computer-readable code on a computer-readable storage medium. The computer-readable storage medium is any data storage device that can store data which can be thereafter read by a computer. Examples of computer-readable storage media include read-only memory (ROM), random-access memory (RAM), CD-ROMs, magnetic tapes, floppy disks, and optical data storage devices. The computer-readable storage media can also be distributed over network coupled computer systems so that computer-readable codes are stored and executed in a distributed fashion.

While preferred exemplary embodiments of the present invention have been described with reference to the figures, it will be understood by one of ordinary skill in the art that various changes in form and details may be made therein without departing from the spirit and scope of the present invention as defined by the following claims. Thus, it should be understood that the exemplary embodiments described therein should be considered in a descriptive sense only and not for purposes of limitation. The scope of the present invention is defined not by the detailed description thereof but by the appended claims, and all differences within the scope of the appended claims and their equivalents will be construed as being included in the present invention.

The invention claimed is:

1. A method of segmenting a human tissue, the method comprising:
   acquiring a three-dimensional (3D) human body image;
   obtaining a first candidate region of a human tissue from the 3D human body image by using a region growing method;
   obtaining a second candidate region of the human tissue based on a directionality of a change in signal intensities of voxels;
   obtaining a third candidate region of the human tissue by using the region growing method to form a single image obtained by combining together the first and second candidate regions;
   segmenting a human tissue region by removing noise based on similarity of a directionality of a change in signal intensity of voxels belonging to the third candidate region; and
   displaying the human tissue region in a output device;
   wherein the acquiring of the 3D human body image comprises obtaining the 3D human body image using computed tomography (CT) scanning or magnetic resonance imaging (MRI).

2. The method of claim 1, wherein the obtaining of the first candidate region comprises obtaining the first candidate region by using the region growing method that grows a region based on an initial upper limit value of signal intensity of a voxel belonging to the human tissue in the 3D human body image.

3. The method of claim 2, wherein the obtaining of the first candidate region comprises:
   decreasing, when a volume of a candidate region obtained by using the region growing method is less than or equal to a reference volume, the initial upper limit value and then obtaining a new candidate region by using again the region growing method based on the decreased upper limit value;
   repeating obtaining of a new candidate region by decreasing the initial upper limit value until a volume of the new candidate region is greater than or equal to the reference volume; and
   determining, when the volume of the new candidate region is greater than or equal to the reference volume, a previously obtained candidate region as the first candidate region.

4. The method of claim 2, wherein the obtaining of the first candidate region comprises:
   decreasing the initial upper limit value;
   calculating a ratio between the number of voxels belonging to a candidate region newly obtained by using the region growing method based on the decreased upper limit value and the number of voxels belonging to a previously obtained candidate region; and
   determining, if the ratio exceeds a preset threshold value, a previously obtained candidate region as the first candidate region.

5. The method of claim 1, wherein the obtaining of the first candidate region further comprises performing a morphological closing operation on the first candidate region by using a structuring element.

6. The method of claim 1, further comprising, before the obtaining of the first candidate region, performing anisotropic diffusion filtering.

7. The method of claim 1, wherein the obtaining of the second candidate region comprises:
   segmenting the human tissue from the 3D human body image by using the region growing method;
   calculating a first eigenvector and a first eigenvalue for a change in signal intensity of voxels belonging to the human tissue in each direction; and
   obtaining the second candidate region by comparing the first eigenvector and the first eigenvalue of each of the voxels with a reference eigenvector and a referenced eigenvalue preset for a change in signal intensity of a human tissue structure.

8. The method of claim 7, wherein, in the obtaining of the second candidate region, eigenvalues $\lambda 1$, $\lambda 2$, and $\lambda 3$ corresponding to three directions of each of the voxels satisfy a condition in which $\lambda 1$ is less than the reference eigenvalue and $\lambda 2$ and $\lambda 3$ are greater than the reference eigenvalue.

9. The method of claim 1, wherein the removing of the noise comprises calculating similarity between a vector representing a change in signal intensity of a voxel in the third candidate region and an average vector for a change in signal intensity in a neighboring space including the voxel and considering the voxel having similarity less than or equal to a preset value as noise and removing the voxel.

10. The method of claim 9, wherein the removing of the noise comprises:
    calculating first similarity between a vector of a first voxel in a difference (−) image between the second and first candidate regions and an average vector for a neighboring region of a voxel in the first candidate region that is at the same position as the first voxel and obtaining a fourth candidate region by considering the first voxel having the first similarity less than or equal to a specific value as noise and removing the first voxel;
    calculating second similarity between a vector of a second voxel in a difference (−) image between the third and first candidate regions and an average vector for a neighboring region of a voxel that is at the same position in the difference (−) image between the second and first candidate regions as the second voxel and obtaining a fifth candidate region by considering the second voxel having the second similarity less than or equal to a specific value as noise and removing the second voxel;
    calculating third similarity between a vector of a third voxel in an intersection region composed of voxels belonging to the third candidate region, voxels not belonging to the fourth candidate region, and voxels not belonging to the fifth candidate region and an average vector for a neighboring region of a voxel that is at the same position in the difference (−) image between the fifth and first candidate regions as the third voxel and segmenting the airway region by restoring voxels having the third similarity greater than or equal to a specific value.

11. The method of claim 10, wherein the segmenting of the human tissue region further comprises removing an island having less than a preset number of voxels among islands obtained by performing 3D labeling on the segmented human tissue and connecting and restoring an island having a number of voxels that are greater than or equal to the preset number of voxels based on the third candidate region.

* * * * *